(12) United States Patent
Murer et al.

(10) Patent No.: US 7,687,657 B2
(45) Date of Patent: Mar. 30, 2010

(54) PROCESS FOR PREPARING ACYLPHOSPHANES AND DERIVATIVES THEREOF

(75) Inventors: Peter Murer, Oberwill (CH); Jean-Pierre Wolf, Maisprach (CH); Stephan Burkhardt, Gelterkinden (CH); Hansjörg Grützmacher, Dielsdorf (CH); Daniel Stein, Horw (CH); Kurt Dietliker, Allschwil (CH)

(73) Assignee: Ciba Speciality Chemicals Corporation, Tarrytown, NY (US)

( * ) Notice: Subject to any disclaimer, the term of this patent is extended or adjusted under 35 U.S.C. 154(b) by 0 days.

(21) Appl. No.: 11/667,780

(22) PCT Filed: Nov. 14, 2005

(86) PCT No.: PCT/EP2005/055935

§ 371 (c)(1),
(2), (4) Date: May 15, 2007

(87) PCT Pub. No.: WO2006/056541

PCT Pub. Date: Jun. 1, 2006

(65) Prior Publication Data

US 2008/0004464 A1 Jan. 3, 2008

(30) Foreign Application Priority Data

Nov. 23, 2004 (EP) .................. 04105987

(51) Int. Cl.
*C07C 69/76* (2006.01)
*C07C 69/95* (2006.01)

(52) U.S. Cl. .............. 560/51; 568/15; 568/12; 568/13

(58) Field of Classification Search ........... 560/51; 568/12, 13, 15
See application file for complete search history.

(56) References Cited

U.S. PATENT DOCUMENTS

| | | | |
|---|---|---|---|
| 3,397,039 A | 8/1968 | Peterson | 23/204 |
| 3,723,536 A | 3/1973 | Stuebinger et al. | 260/606.5 |
| 4,792,632 A * | 12/1988 | Ellrich et al. | 568/15 |
| 5,218,009 A * | 6/1993 | Rutsch et al. | 522/16 |
| 6,399,805 B2 * | 6/2002 | Wolf et al. | 556/405 |
| 6,579,663 B2 * | 6/2003 | Wolf et al. | 430/281.1 |
| 6,888,031 B1 * | 5/2005 | Leppard et al. | 568/14 |
| 2005/0283027 A1 | 12/2005 | Grutzmacher et al. | 568/9 |
| 2006/0229469 A1 * | 10/2006 | Huttenloch et al. | 562/876 |
| 2006/0247436 A1 * | 11/2006 | Sommerlade et al. | 544/157 |

FOREIGN PATENT DOCUMENTS

| | | |
|---|---|---|
| DE | 20 07 535 | 9/1971 |
| EP | 0 040 721 | 12/1981 |
| EP | 495751 * | 7/1992 |
| EP | 1 135 399 | 8/2002 |
| JP | 47041114 * | 10/1972 |
| WO | 00/32612 | 6/2000 |
| WO | 2005/014605 | 2/2005 |
| WO | WO 2005/014605 * | 2/2005 |
| WO | 2005/037763 | 4/2005 |

OTHER PUBLICATIONS

Becker et al., Syntheses and properties of acylphosphanes. V. tert-Butyl- and phenylpivaloylphosphanes, Zeitschrift fuer Anorganische und Allgemeine Chemie (1978), 439, 121-133. Abstract.*

(Continued)

*Primary Examiner*—Porfirio Nazario Gonzalez
*Assistant Examiner*—Chukwuma O Nwaonicha
(74) *Attorney, Agent, or Firm*—Joseph C. Suhadolnik

(57) ABSTRACT

The invention relates to a process for the preparation of (bis) acylphosphanes of formula I, wherein n and m are each independently of the other 1 or 2; R1 if n=1, is e.g. unsubstituted or substituted $C_1$-$C_{18}$alkyl or $C_2$-$C_{18}$alkenyl, or phenyl, R1 if n=2, is e.g. a divalent radical of the monovalent radical defined above; R2 is e.g. $C_1$-$C_{18}$alkyl, $C_3$-$C_{12}$cycloalkyl, $C_2$-$C_{18}$alkenyl, mesityl, phenyl, naphthyl; R3 is one of the radicals defined under $R_1$; the process comprises the steps a) contacting e.g. elemental phosphorous [P]∞, P(Hal)₃ with a reducing metal optionally in the presence of a catalyst or an activator in a solvent to obtain metal phosphides Me₃P or Me'₃P₂, wherein Me is an alkali metal and Me' is an earth alkali metal or to obtain metal polyphosphides b) optionally adding a proton source, optionally in the presence of a catalyst or an activator to obtain metal dihydrogen phosphides MePH₂; c) subsequent acylation reaction with m acid halides of formula III or m carboxylic acid esters of formula IV or, in case that in formula I m=1, with one carboxylic ester of formula IV followed by one acid halide of formula III or vice versa, wherein R is the residue of an alcohol and $R_2$ is as defined above; d) alkylation reaction subsequent reaction with an electrophilic agent $R_1$Hal or other electrophilic agents to obtain the compounds of formula I. An oxidation step may follow to obtain mono- and bisacylphosphane oxides or mono- and bisacylphosphane sulfides, which are used as photoinitiators.

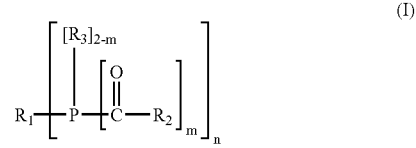

(I)

8 Claims, No Drawings

OTHER PUBLICATIONS

Becker et al., Syntheses properties of acylphosphines. III. Molecular and crystal structure of dipivaloylphosphine, Zeitschrift fuer Anorganische und Allgemeine Chemie (1977), 430, 77-90. Abstract.*

Tyka, A new case of a Friedel-Crafts reaction, Bulletin de l'Academie Polonaise des Sciences, Serie des Sciences Chimiques (1961), 9(9), 575-6. Abstract.*

Frank et al., Tricarbethoxyphosphine, Journal of Organic Chemistry (1971), 36(22), 3461-3464. Abstract.*

Veits et al., Alkylation of the P:C:O triad of organometallic derivatives of alkyl(acyl)phosphines, Zhurnal Organicheskoi Khimii (1996), 32(10), 1570-1572.*

Liotta et al., The synthesis and reactions of potassium benzoylphosphide, benzoylphosphine, and benzoylmethylphosphine, Tetrahedron Letters (1984), 25(12), 1249-1252.*

Veits et al. Aromatic nucleophilic substitution in pentafluoropyridine by three-coordinate phosphorus compounds, Russian Journal of Organic Chemistry (Translation of Zhurnal Organicheskoi Khimii) (2000), 36(5), 750-756.*

Beilstein Institute for Organic Chemistry, XP002366523 Database accession No. BRN 4861648 abstract & VEITS, Yu. A. et al.: J. Ben. Chem. USSR, vol. 61, No. 1.1, 1991, pp. 114-118.

Beilstein Institute for Organic Chemistry, XP002366524 Database accession No. BRN 4741602 abstract & Veits, Yu. A. et al.: J. Ben. Chem. USSR, vol. 60, No. 9.1, 1990, pp. 1810-1816.

Beilstein Institute for Organic Chemistry, XP002366525 BRN 6408435; BRN 6397316; BRN 6402827; BRN 6401300; BRN 6403037 abstract & Thamm, R. et al.: Z. Naturforsch. B Anorg. Chem. Org. Chem., vol. 37, No. 8, 1982, pp. 965-974.

Beilstein Institute for Organic Chemistry, XP002366526 Database accession No. BRN 4707239; BRN 4618627 abstract & Podlahova, J. et al.: Collect Czech Comm, vol. 48, No. 9, 1983, pp. 2604-2606.

Frank, A. et al.: 1, 11 "Tn carbethoxyphosphi ne" J. Org. Chem., vol. 36, No. 22, 1971, pp. 3461-3464, XP002366517 p. 3462, col. 1.

Issleib, K.; Priebe, E.: "Darstellung und 11 Charkteri sierung disubstituierter Sáurephosphide" Chem. Ber., vol. 92, 1959, pp. 3183-3189, XP002260971.

Beilstein Institute for Organic Chemistry, XP002366527 Database accession No. BRN 2364021 abstract & Issleib et al.: Z. Naturforsch. Anorg. Chem. Org. Chem. Biophys. Biol., vol. 22, 1967, pp. 784-785.

Derwent Abst. No. 91349 of EP 40 721.

M. Van Hooijdonk et al., Phosphorus, Sulfur and Silicon, 2000, vol. 162, pp. 39-49.

Steinicke et al, Z. Anorg. Allg. Chem. 623 (1997) pp. 1925-1930.

* cited by examiner

PROCESS FOR PREPARING ACYLPHOSPHANES AND DERIVATIVES THEREOF

The present invention relates to a new, selective process for the preparation of mono- and bisacylphosphanes, mono- and bisacylphosphane oxides or mono- and bisacylphosphane sulfides starting from elemental phosphorous $[P]_\infty$ or phosphorous reagents with a formal oxidation state of phosphorous $>-3$, such as for example phosphorous trihalogenide $P(Hal)_3$ or, phosphorous oxides without isolation of the intermediates.

As the technology of the mono- and bisacylphosphine oxides is becoming increasingly important owing to the excellent photoinitiator properties of these compounds there is also a need for highly practicable processes involving as little elaboration for the preparation of the required intermediates, especially of the corresponding mono- and bisacylphosphanes, but also of the oxide and sulfide end products. There still remains a need for a process which allows a high variability and flexibility for the introduction of all three substituents at the phosphorous atom of mono- and bisacylphosphane structures.

The European Patent Publication EP1 135 399 B1 describes a process for the preparation of mono- and bisacylphosphanes, of mono- and bisacylphosphane oxides and of mono- and bisacylphosphane sulfides, which process comprises first reacting organic P-monohalogenophosphanes ($R_2$—PCl) or P,P-dihalogenophosphanes (R—$PCl_2$) or mixtures thereof, with an alkali metal or magnesium in combination with lithium, where appropriate in the presence of a catalyst, and then carrying out the reaction with acid halides and, in the case of the process for the preparation of oxides, carrying out an oxidation step and, in the case of the preparation of sulfides, reacting the phosphanes so obtained with sulfur. The reaction is usefully carried out in a solvent. The solvent used may be, in particular, ethers which are liquid at normal pressure and room temperature. Examples thereof are dimethyl ether, diethyl ether, methylpropyl ether, 1,2-dimethoxyethane, bis(2-methoxyethyl)ether, dioxane or tetrahydrofuran. Tetrahydrofuran is preferably used.

The International Application PCT/EP 04/51427 describes a process to prepare mono- and bisacylphosphanes, which process comprises first reacting organic P-monohalogenophosphanes ($R_2$—PCl) or P,P-dihalogenophosphanes (R—$PCl_2$), or phosphorous halide oxide or phosphorous halide sulfide with an alkali metal (metallation) in a solvent in the presence of a proton source (reduction), and where appropriate in the presence of a catalyst, and then carrying out the reaction with acid halides.

Brandsma and coworkers describe the preparation of dihydrogen metal phosphides, represented by the formula $MePH_2$, by the reaction of $Me_3P$ with a proton source (tert-butanol) in an organic solvent, preferably THF or DME (M. C. J. M. van Hoijdonk, G. Gerritsen, L. Brandsma, Phosphorous, Sulfur, Silicon 2000, 162, 39-49). Addition of an alkyl halide RHal leads to the formation of a monoalkyl phosphine $RPH_2$. It is known that monoalkyl phosphines can be further reacted with an acid halide, as described in the International Application PCT/EP 04/51427, filed Jul. 9, 2004.

A. Steinicke and coworkers describe the reduction of red phosphorous with strongly reducing metals, giving metal phosphides $Me_nP_m$. Addition of an alkyl halide leads to the formation of alkylcyclophosphanes cyclo-$(RP)_n$ (A. Steinicke, K.-H. Thiele, A. Haaland, V. I. Sokolov, H. V. Volden, Z. anorg. alig. Chem. 1997, 623, 1925-1930). Reductive cleavage of alkylcyclophosphanes with a metal in the presence of a proton source (e.g. tert-butanol) gives a monoalkyl phosphine $RPH_2$, which can be further reacted with an acid halide, as described in the International Application PCT/EP 04/51427.

The above referenced patent publications describe a process wherein the alkyl or aryl substituent at the phosphorous atom of the mono- or bisacylphosphane was part of the starting material $R_2$—PCl or R—$PCl_2$. As only a limited number of P-monohalogenophosphanes ($R_2$—PCl) or P,P-dihalogenophosphanes (R—$PCl_2$) are readily available, accessible, or processable, there is a need to develop a process enabling the preparation of mono- and bisacylphosphanes which process provides a higher variance for the substituents at the phosphorous atom. Furthermore, it should be avoided to use toxic, pyrophoric and difficult to handle phosphorous starting materials, like phosphine gas ($PH_3$), or primary and secondary alkyl and aryl phosphines R—$PH_2$, $R_2$—PH, respectively.

Photoinitiators bearing suitable functional groups that allow a chemical reaction with suitable functional groups on low molecular, oligomeric or polymeric compounds are highly demanded for the development of compositions containing low volatile and non-migrating photoinitiators, as they are for examples required for printing inks used in direct food contact applications. Furthermore, photoinitiators bearing suitable functional groups can be linked to other additives, such as sensitizers, stabilizers, surface active agents and so on, in order to provide an additional functionality to the photoinitiator. Hence an easy access to such functionalized photoinitiators, especially mono- or bisacylphosphine oxides, is highly desirable In the above mentioned patent publications, the acylation of the intermediate primary or secondary alkyl and aryl phosphines R—$PH_2$ and $R_2$—PH, respectively, is performed in the presence of strong bases, such as butyl lithium, or alkali metals such as lithium or sodium. Many functional groups do not tolerate such reaction conditions. Hence the type of functional groups that can be introduced on the residue R by the processes claimed in the aforementioned patents is limited to those that tolerate these harsh reaction conditions. Therefore, there is a need for a synthetic access that allows the easy introduction of a broader variety of functional groups on the substituents on the phosphorous atom.

It has now been found that in the process according to the invention a reactive intermediate is generated, which can selectively be alkylated/arylated using any alkylating/arylating agent (e.g. RHal), or reacted with typical electrophiles. The substituent R at the phosphorous atom is thus introduced via a reaction with an electrophile within the said process. The possibility of using any electrophile provides a higher variance for the substituents at the phosphorous atom.

Furthermore, said substituent R is introduced after the acylation step that requires the use of strong bases, such as butyl lithium, or of alkali metals, such as lithium or sodium. Thus even substituents bearing functional groups that would not tolerate such conditions can be introduced, thereby considerably enlarging the variance of functional groups.

Starting with the reduction of elemental phosphorous $[P]_\infty$, phosphorous trihalogenide $P(Hal)_3$, or other phosphorous compounds possessing a phosphorous atom with a formal oxidation state $>-3$, followed by the acylation of the obtained metal phosphides $Me_nP_m$[e.g. trialkali metal phosphide ($Me_3P$)], or the acylation of dihydrogen metal phosphide ($MePH_2$), it is possible to avoid the use, the isolation, the generation, or the handling of a toxic gas like $PH_3$, or alkyl and aryl phosphines. The whole process may optionally be performed in the same reactor ("one-pot" reaction).

The invention relates to a process for the preparation of acylphosphanes or bisacylphosphanes of formula I

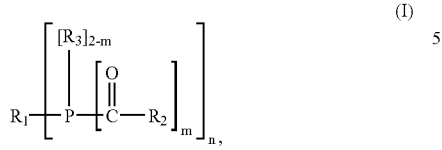 (I)

wherein n and m are each independently of the other 1 or 2;

$R_1$ if n=1, is unsubstituted linear or branched $C_1$-$C_{18}$alkyl or $C_2$-$C_{18}$alkenyl; or linear or branched $C_1$-$C_{18}$alkyl or $C_2$-$C_{18}$alkenyl substituted once or more than once by groups selected from:

halogen or CN, or

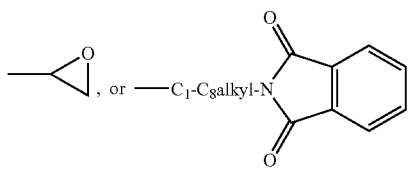

—$OR_{10}$, —$SR_{10}$, —OCO—$R_{10}$, —COO—$R_{10}$, —CH=CH—CO—$OR_{10}$ or —C($C_1$-$C_4$alkyl)=C($C_1$-$C_4$alkyl)-CO—$OR_{10}$; wherein $R_{10}$ is hydrogen, $C_1$-$C_{18}$alkyl, or $C_2$-$C_{18}$alkyl which is interrupted by one or several non-successive —O-atoms, a di, -tri, -tetra- or polyethylene glycol residue, $C_3$-$C_{12}$-cycloalkyl, tetrahydropyran-2-yl, phenyl-$C_1$-$C_4$-alkylene, phenyl-$C_1$-$C_4$-alkenylene, $C_1$-$C_6$alkyl substituted by halogen or substituted by cyclohexyl or cyclopentyl, or substituted by tetrahydrofuranyl, furanyl, isopropyl-4-methyl-cyclohexyl, $C_2$-$C_{18}$-alkenyl, unsubstituted phenyl, naphthyl or biphenyl being unsubstituted or phenyl, naphthyl or biphenyl substituted by one to five $C_1$-$C_8$-alkyl, $C_1$-$C_8$-alkoxy, $C_1$-$C_8$-alkylthio and/or halogen; or $R_1$ is linear or branched $C_1$-$C_{18}$alkyl or $C_2$-$C_{18}$alkenyl substituted by —CO—$R_{11}$; wherein $R_{11}$ is $C_1$-$C_{18}$alkyl, or $C_2$-$C_{18}$alkyl which is interrupted by one or several non-successive —O-atoms, $C_3$-$C_{12}$-cycloalkyl, phenyl-$C_1$-$C_4$-alkylene, unsubstituted phenyl, naphthyl or biphenyl being unsubstituted or phenyl, naphthyl or biphenyl substituted by one to five $C_1$-$C_8$-alkyl, $C_1$-$C_8$-alkoxy, $C_1$-$C_8$-alkylthio and/or halogen or $R_1$ is linear or branched $C_1$-$C_{18}$alkyl or $C_2$-$C_{18}$alkenyl substituted by —CO—$(CH)_2$—CO—$C_1$-$C_6$alkyl, CO—$(CH)_2$—CO-phenyl, or by CO—$(CH)_2$—COO—$C_1$-$C_{18}$alkyl; or $R_1$ is linear or branched $C_1$-$C_{18}$alkyl or $C_2$-$C_{18}$alkenyl substituted by —$NR_{12}R_{13}$, —$N(R_{12})$—CO—$R_{10}$, —$N(R_{12})$—CO—$OR_{10}$, —$N(R_{12})$—CO—$NR_{12}R_{13}$, —$N(R_{12})$—CO-Hal, —CO—$NR_{12}R_{13}$, wherein $R_{10}$ is as defined above and $R_{12}$ and $R_{13}$ independently of one another are is hydrogen, $C_1$-$C_{18}$alkyl, $C_2$-$C_{18}$alkyl which is interrupted by one or several non-successive O atoms, $C_3$-$C_{12}$-cycloalkyl, $C_2$-$C_{18}$-alkenyl, phenyl-$C_1$-$C_4$-alkyl, phenyl, naphthyl, pyridyl, the radicals phenyl, naphthyl or pyridyl being unsubstituted or substituted by one to five $C_1$-$C_8$-alkyl, $C_1$-$C_8$-alkoxy, $C_1$-$C_8$-alkylthio and/or halogen; or $R_{12}$ and $R_{13}$ forms a 5- or 6-membered O—, S— or N-containing heterocyclic ring; that may be further annelated by an aliphatic or aromatic ring; or —$SO_2$—$R_{10}$, —$SO_2$—$OR_{10}$, —$SO_2$—$NR_{12}R_{13}$, wherein $R_{10}$, $R_{12}$ and $R_{13}$ are as defined above; or —PO(O$C_1$-$C_8$alkyl)$_2$, or —$SiR_{14}R_{15}R_{16}$, wherein $R_{14}$, $R_{15}$ and $R_{16}$ independently of one another are H, $C_1$-$C_8$alkyl, $C_2$-$C_8$alkenyl, phenyl, $C_7$-$C_9$phenylalkyl, —O$C_1$-$C_8$alkyl, —O—$SiR_{17}R_{18}R_{19}$, wherein $R_{17}$, $R_{18}$ and $R_{19}$ are independently of each other H, $C_1$-$C_8$alkyl, $C_2$-$C_8$alkenyl, phenyl, $C_7$-$C_9$phenylalkyl, —O$C_1$-$C_8$alkyl; or —CH=CH-phenyl or —C($C_1$-$C_4$alkyl)=C($C_1$-$C_4$alkyl)-phenyl, phenyl-$C_1$-$C_4$alkyl, phenyl, naphthyl, biphenyl, $C_5$-$C_{12}$cycloalkyl or a 5- or 6-membered O-, S- or N-containing heterocyclic, ring; benzophenonyl, thioxanthonyl; or $R_1$ is $C_2$-$C_{18}$alkyl or $C_2$-$C_{18}$alkenyl which is interrupted by one or several non-successive —O—, —NH—, —$NR_{12}$— or —S— atoms, and may additionally be substituted once or more than once by groups selected from:

halogen or CN, or

—$OR_{10}$, —$SR_{10}$, —OCO—$R_{10}$, —COO—$R_{10}$, wherein $R_{10}$ is as defined above; or —$NR_{12}R_{13}$, —$N(R_{12})$—CO—$R_{10}$, —$N(R_{12})$—CO—$OR_{10}$, —$N(R_{12})$—CO—$NR_{12}R_{13}$, —$N(R_{12})$—CO-Hal, —CO—$NR_{12}R_{13}$, wherein $R_{10}$ and $R_{12}$ and $R_{13}$ are as defined above; or —$SO_2$—$R_{10}$, —$SO_2$—$OR_{10}$, —$SO_2$—$NR_{12}R_{13}$, wherein $R_{10}$, $R_{12}$ and $R_{13}$ are as defined above; or —PO(O$C_1$-$C_8$alkyl)$_2$, or —$SiR_{14}R_{15}R_{16}$, wherein $R_{14}$, $R_{15}$ and $R_{16}$ are as defined above; or phenyl-$C_1$-$C_4$alkyl, phenyl or $C_5$-$C_{12}$cycloalkyl; or $R_1$ is $C_2$-$C_{18}$alkyl or $C_2$-$C_{18}$alkenyl which is interrupted by —CO—, —COO—, —OCO—, —OCOO—, —CO—N($R_{12}$)—, —N($R_{12}$)—CO—, —N($R_{12}$)—CO—N($R_{12}$)—, —N($R_{12}$)—COO—, —COO—$C_1$-$C_{18}$alkylene, —COS—$C_1$-$C_{18}$alkylene, —$SO_2$—, —$SO_2$—O—, —$SO_2$—N($R_{12}$)—, —(CH$_3$)$_2$Si—[OSi(CH$_3$)$_2$]$_m$— with m=1-6, phenyl-$C_1$-$C_4$alkylene, phenylene, naphthylene, biphenylene, $C_5$-$C_{12}$cycloalkylene or a 5- or 6-membered O-, S- or N-containing heterocyclic ring; wherein $R_{12}$ is as defined above; or $R_1$ is trimethylsilyl or Hal-(CH$_3$)$_2$Si—[OSi(CH$_3$)$_2$]$_m$— or (CH$_3$)$_3$Si—[OSi(CH$_3$)$_2$]$_m$— with m=1-6; or $R_1$ is —COOH, —COO—$R_{10}$, —CO—$NR_{12}R_{13}$, —CO-vinyl, —CO-phenyl which is unsubstituted or substituted by one or more —CH$_3$, —OCH$_3$, —Cl; wherein $R_{10}$, $R_{12}$ and $R_{13}$ are as defined above; or $R_1$ is phenyl-$C_1$-$C_4$alkyl, phenyl, naphthyl, biphenyl, $C_5$-$C_{12}$cycloalkyl or a 5- or 6-membered O-, S- or N-containing heterocyclic ring; all of the radicals phenyl, naphthyl, biphenyl, $C_5$-$C_{12}$cycloalkyl or the 5- or 6-membered —O-, S- or N-containing heterocyclic ring being unsubstituted or substituted by one to five halogen, $C_1$-$C_8$alkyl, $C_1$-$C_8$alkylthio, $C_1$-$C_8$alkoxy and/or —$NR_{12}R_{13}$; wherein $R_{12}$ and $R_{13}$ are as defined above;

$R_1$ if n=2, is a divalent radical of the monovalent radical defined above or is

-continued

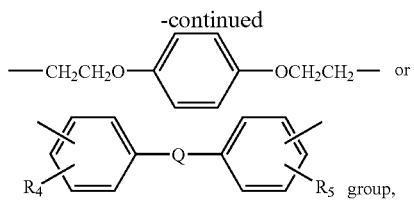

—CH$_2$—COO-Z-OCO—CH$_2$— wherein

Q is a single bond, —CH$_2$—, —CR$_6$R$_7$—, —O— or —S—; R$_4$ and R$_5$ are each independently of the other hydrogen, C$_1$-C$_4$alkyl or C$_1$-C$_4$alkoxy; R$_6$ and R$_7$ are each independently of the other C$_1$-C$_4$alkyl;

Z is C$_1$-C$_{18}$ alkylene or a bridge derived from a di, -tri, -tetra- or polyethylene glycol.

R$_2$ is C$_1$-C$_{18}$alkyl or C$_2$-C$_{18}$alkeny; C$_1$-C$_{18}$alkyl or C$_2$-C$_{18}$alkenyl substituted once or more than once by halogen; or —OR$_{10}$, —OCO—R$_{10}$, —OCO-Hal, —COO—R$_{10}$, —CH═CH—CO—OR$_{10}$—N(R$_{12}$)—CO—R$_{10}$, —N(R$_{12}$)—CO-Hal; —C(C$_1$-C$_4$alkyl)═C(C$_1$-C$_4$alkyl)-CO—OR$_{10}$, —CO—NR$_{12}$R$_{13}$, wherein R$_{10}$, R$_{12}$ and R$_{13}$ are as defined above; or —CH═CH-phenyl or —C(C$_1$-C$_4$alkyl)═C(C$_1$-C$_4$alkyl)-phenyl;

C$_3$-C$_{12}$cycloalkyl, C$_2$-C$_{18}$alkenyl, phenyl-C$_1$-C$_4$alkyl, phenyl, naphthyl, anthryl. biphenyl or a 5- or 6-membered —O-, S- or N-containing heterocyclic ring, the radicals phenyl, naphthyl, biphenyl or the 5- or 6-membered —O-, S- or N-containing heterocyclic ring being unsubstituted or substituted by one to five halogen, C$_1$-C$_8$alkyl, C$_1$-C$_8$alkoxy and/or C$_1$-C$_8$alkylthio;

R$_3$ is one of the radicals defined under R$_1$;

the process comprises the steps a) contacting elemental phosphorous [P]$_\infty$, P(Hal)$_3$ or other phosphorous compounds in which the formal oxidation state of the phosphorous atom is higher than (−3) with a reducing metal optionally in the presence of a catalyst or an activator in a solvent to obtain metal phosphides Me$_3$P or Me'$_3$P$_2$, wherein Me is an alkali metal and Me' is an earth alkali metal or to obtain metal polyphosphides, b) optionally adding a proton source, optionally in the presence of a catalyst or an activator to obtain metal dihydrogen phosphides MePH$_2$;

c) subsequent acylation reaction with m acid halides of formula III or m carboxylic acid esters of formula IV

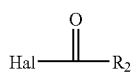 (III)

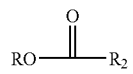 (IV)

or, in case that in formula I m=1, with one carboxylic ester of formula IV followed by one acid halide of formula III or vice versa, wherein R is the residue of an alcohol and R$_2$ is as defined above;

d) alkylation reaction in case of m=2, subsequent reaction with an electrophilic agent R$_1$Hal or other electrophilic agents such as R$_1$—OSO$_2$—O—R$_1$, R$_1$—OSO$_2$—R$_{20}$,

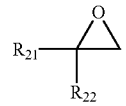

(R$_1$—O)$_3$PO, H$_2$C═CR$_{23}$COOR$_{10}$,

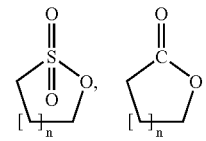

wherein R$_1$ and R$_{10}$ are as defined above, R$_{20}$ is C$_1$-C$_8$-alkyl, C$_1$-C$_8$-perfluoroalkyl, aryl or C$_1$-C$_4$-alkylaryl, R$_{21}$ is H or C$_1$-C$_8$alkyl; R$_{22}$ is C$_1$-C$_{16}$alkyl or C$_2$-C$_{16}$alkenyl substituted once or more than once by halogen —OR$_{10}$, —NR$_{12}$R$_{13}$, —SR$_{10}$, —OCO—R$_{10}$, —OCO-Hal, —COO—R$_{10}$, —N(R$_{12}$)—CO—R$_{10}$, —N(R$_{12}$)—CO—OR$_{10}$, —N(R$_{12}$)—CO—NR$_{12}$R$_{13}$, —N(R$_{12}$)—CO-Hal, —CO—NR$_{12}$R$_{13}$, —SO$_2$—R$_{10}$, —SO$_2$—OR$_{10}$, —SO$_2$—NR$_{12}$R$_{13}$, —CH═CH—CO—OR$_{10}$, —CH═CH-phenyl, —C(C$_1$-C$_4$alkyl)═C(C$_1$-C$_4$alkyl)-CO—OR$_{10}$ or —C(C$_1$-C$_4$alkyl)═C(C$_1$-C$_4$alkyl)-phenyl, phenyl-C$_1$-C$_4$alkyl, phenyl, naphthyl, biphenyl, C$_5$-C$_{12}$cycloalkyl or a 5- or 6-membered O—, S— or N-containing heterocyclic ring; R$_{23}$ is H or CH$_3$, and n=1-5 and R$_{10}$, R$_{12}$ and R$_{13}$ is as defined above;

and in the case of m=1 reaction with an electrophilic agent R$_1$Hal or other electrophilic agents such as R$_1$—OSO$_2$—O—R$_1$, R$_1$—OSO$_2$—R$_{20}$,

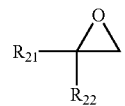

(R$_1$—O)$_3$PO, H$_2$C═CR$_{23}$COOR$_{10}$,

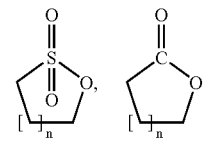

wherein R$_1$ and R$_{10}$; R$_{20}$, R$_{21}$, R$_{22}$ and R$_{23}$ are as defined above followed by the reaction with an electrophilic agent R$_3$Hal or other electrophilic agents such as R$_3$—OSO$_2$—O—R$_3$, R$_3$—OSO$_2$—R$_{20}$,

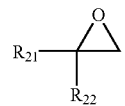

(R$_3$—O)$_3$PO, H$_2$C═CR$_{23}$COOR$_{10}$,

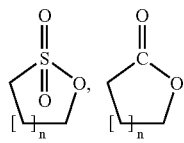

wherein $R_3$ and $R_{10}$, $R_{20}$, $R_{21}$, $R_{22}$ and $R_{23}$ are as defined above to obtain the compounds of formula I.

The subsequent reaction of the intermediate obtained according to c) can also be performed under typical conditions known in the art for enolates such as radical or metal-promoted addition reactions, such as a palladium-catalyzed reaction with $R_1$Hal, in which $R_1$ is an unsubstituted or substituted aryl group.

The subsequent reaction can also include first a protonation reaction of the enolate, followed by a subsequent radical or metal-promoted addition reaction with $R_1$Hal, where $R_1$ is an unsubstituted or substituted aryl group.

In another of its aspect, this invention relates to a process for the preparation of monoacylphosphanes of the formula I' (compounds of the formula I with n=1 and m=1)

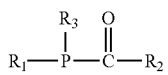
(I')

wherein $R_1$, $R_2$ and $R_3$ are as defined in claim 1, which process comprises the steps a), b) and c) as defined in claim 1; and d) reaction with an electrophilic agent $R_1$Hal or other electrophilic agents containing the residue $R_1$ as defined in claim 1 step d for m=1 followed by the reaction with an electrophilic agent $R_3$Hal or other electrophilic agents containing the residue $R_3$ as defined in claim 1 step d for m=1 to obtain the compounds of formula I'.

In another of its aspect, this invention relates to a process for the preparation of symmetric bisacylphosphanes of the formula I'' (compounds of the formula I with n=1 and m=2)

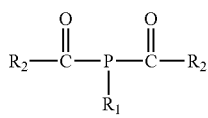
(I'')

wherein $R_1$ and $R_2$ are as defined in claim 1, which process comprises the steps a), b) and c) as defined in claim 1 for m=2; and d) reaction with an electrophilic agent $R_1$Hal or other electrophilic agents containing the residue $R_1$ as defined in claim 1 step d for m=2 to obtain the compounds of formula I''.

In another of its aspect, this invention relates to a process for the preparation of unsymmetric bisacylphosphanes of the formula I''' (compounds of the formula I with n=1 and m=2)

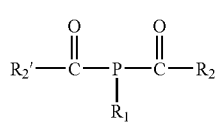
(I''')

wherein $R_1$ is as defined in claim 1 and $R_2$ and $R_2'$ independently of one another are as defined in claim 1 under $R_2$ with the proviso that $R_2$ is not equal $R_2'$, which process comprises the steps a) and b) as defined in claim 1; and c) subsequent reaction with an acid halide of formula III or a carboxylic acid ester of formula IV

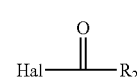
(III)

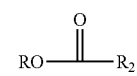
(IV)

wherein R is the residue of an alcohol and $R_2$ is as defined in claim 1;

subsequent reaction with a second acid halide III' or a second carboxylic acid ester of the formula IV',

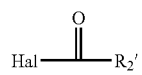
(III')

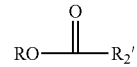
(IV')

wherein $R_2'$ and Hal are as defined above.

d) reaction with an electrophilic agent $R_1$Hal or other electrophilic agents containing the residue $R_1$ as defined in claim 1 step d for m=2 to obtain the compounds of formula I'''.

In another of its aspect, this invention also relates to a process for the preparation of symmetric metal bisacylphosphides of the formula (V) or (Va)

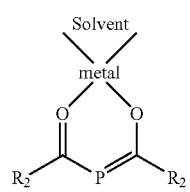
(V)

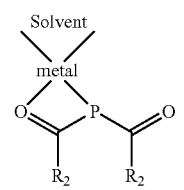
(Va)

wherein $R_2$ is as defined in claim 1 and the metal is Li, Na, K, Mg, which process comprises the steps a) b) and c) as defined in claim 1 for m=2.

In another of its aspect, this invention also relates to a process for the preparation of unsymmetric metal bisacylphosphides of the formula (V') or (Va')

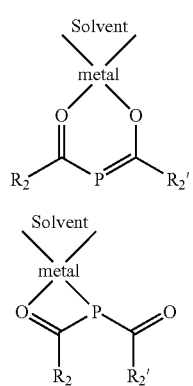

wherein $R_2$ and $R_2'$ are as defined in claim 4 and the metal is Li, Na, K, Mg, which process comprises the steps a) b) and c) as defined in claim 4.

In another of its aspects, this invention relates to a process for the preparation of (bis)acylphosphane oxides and (bis)acylphosphane sulfides of formula VI

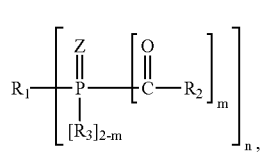

wherein
$R_1$, $R_2$, $R_3$, n and m are as defined above, and Z is O or S, by oxidation or reaction with sulfur of the acylphosphane of formula I, I', I'' or I'''.

Definitions:

$C_1$-$C_{18}$Alkyl is linear or branched and is, for example, $C_1$-$C_{12}$-, $C_1$-$C_8$-, $C_1$-$C_6$- or $C_1$-$C_4$alkyl. Examples are methyl, ethyl, propyl, isopropyl, n-butyl, sec-butyl, isobutyl, tert-butyl, pentyl, hexyl, heptyl, 2,4,4-trimethylpentyl, 2-ethylhexyl, octyl, nonyl, decyl, undecyl, dodecyl, tetra-decyl, pentadecyl, hexadecyl, heptadecyl or octadecyl.

$C_2$-$C_{18}$Alkyl or $C_2$-$C_{18}$alkenyl which is interrupted once or several times by non-successive —O—, —NH—, —NR$_9$—, —S-atoms is interrupted, for example, 1-9, e.g. 1-7, 1-5, 1-3 or 1 or 2, times by —O—, —NH—, —NR$_{12}$—, —S— atoms, the —O—, —NH—, —NR$_{12}$—, —S-atoms always being interrupted by at least one methylene group. The alkyl groups or alkenyl groups may be linear or branched. The structural units obtained are thus, for example, —CH$_2$—X—CH$_3$, —CH$_2$CH$_2$—X—CH$_2$CH$_3$, —[CH$_2$CH$_2$X]$_y$CH$_3$, where y=1-8, —(CH$_2$CH$_2$X)$_7$CH$_2$CH$_3$, —CH$_2$—CH(CH$_3$)—X—CH$_2$—CH$_2$CH$_3$ or —CH$_2$—CH(CH$_3$)—X—CH$_2$—CH$_3$ with X=—O—, —S—, —NH—, —NR$_{12}$— and the corresponding alkenyl structures.

Examples for $C_2$-$C_{18}$alkyl or $C_2$-$C_{18}$alkenyl which is interrupted by —CO—, —COO—, —OCO—, —OCOO—, —CO—N(R$_{12}$)—, —N(R$_{12}$)—CO—, —N(R$_{12}$)—CO—N(R$_{12}$)—, —N(R$_{12}$)—COO—, —COO—C$_1$-C$_{18}$alkylene, —COS—C$_1$-C$_{18}$alkylene, —SO$_2$—, —SO$_2$—O—, —SO$_2$—N(R$_{12}$)—, —(CH$_3$)$_2$Si—[OSi(CH$_3$)$_2$]$_m$—, phenyl-C$_1$-C$_4$alkylene, phenylene, naphthylene, biphenylene, $C_5$-$C_{12}$cycloalkylene or a 5- or 6-membered O—, S— or N-containing heterocyclic ring are the following structures —CH$_2$—W—CH$_3$, —CH$_2$CH$_2$—W—CH$_2$CH$_3$, —[CH$_2$CH$_2$W]$_y$CH$_3$, where y=1-8, —(CH$_2$CH$_2$W)$_7$CH$_2$CH$_3$, —CH$_2$—CH(CH$_3$)—W—CH$_2$—CH$_2$CH$_3$, —CH$_2$—W—CH$_2$—CH$_3$, —CH$_2$—W—CH$_3$, —CH$_2$—W—C(CH$_3$)$_3$, —CH(CH$_3$)—W—CH$_2$—CH$_3$, —CH$_2$—CH$_2$—CH$_2$—W—CH$_3$, —(CH$_2$)$_8$—W—CH$_3$, —CH$_2$—CH$_2$—W—CH=CH$_2$, —CH$_2$—CH$_2$—W—C(CH$_3$)=CH$_2$ or —CH$_2$—CH(CH$_3$)—W—CH$_2$—CH$_3$ with W=CO—, —COO—, —OCO—, —OCOO—, —CO—N(R$_{12}$)—, —N(R$_{12}$)—CO—, —N(R$_{12}$)—CO—N(R$_{12}$)—, —N(R$_{12}$)—COO—, —COO—C$_1$-C$_{18}$alkylene, —COS—C$_1$-C$_{18}$alkylene, —SO$_2$—, —SO$_2$—O—, —SO$_2$—N(R$_{12}$)—, —(CH$_3$)$_2$Si—[OSi(CH$_3$)$_2$]$_m$, —(CH$_2$)$_3$—Si—(O—CH$_2$—CH$_3$)$_3$, —CH$_2$—CH$_2$—PO—(O—CH$_2$—CH$_3$)$_2$, phenyl-C$_1$-C$_4$alkylene, phenylene, naphthylene, biphenylene, $C_5$-$C_{12}$cycloalkylene or a 5- or 6-membered O-, S- or N-containing heterocyclic divalent ring, N-phthalimidyl $C_2$-$C_{18}$Alkenyl radicals may be mono- or polyunsaturated, linear or branched, cyclic or bicyclic and are, for example, vinyl, allyl, methallyl, 1,1-dimethylallyl, propenyl, butenyl, pentadienyl, hexenyl octenyl or exo or endo (bicyclo[2.2.1]hept-2-en-5-yl)-methyl preferably vinyl, allyl, 3-buten-1-yl (unser Ex) or exo and endo (bicyclo[2.2.1]hept-2-en-5-yl)-methyl.

$C_5$-$C_{12}$Cycloalkyl is, for example, cyclopentyl, cyclohexyl, cyclooctyl, cyclododecyl, preferably cyclopentyl and cyclohexyl, more preferably cyclohexyl.

$C_1$-$C_8$Alkoxy is linear or branched radicals and is typically methoxy, ethoxy, propoxy, isopropoxy, n-butyloxy, sec-butyloxy, isobutyloxy, tert-butyloxy, pentyloxy, hexyloxy, heptyloxy, 2,4,4-trimethylpentyloxy, 2-ethylhexyloxy or octyloxy, preferably methoxy, ethoxy, propoxy, isopropoxy, n-butyloxy, sec-butyloxy, isobutyloxy, tert-butyloxy, most preferably methoxy.

Phenyl-$C_1$-$C_4$alkyl is e.g., benzyl, phenylethyl, α-methylbenzyl or α,α-dimethylbenzyl, preferably benzyl.

Halogen (=Hal) is fluoro, chloro, bromo and iodo, preferably chloro and bromo, most preferably chloro.

In the group —NR$_{12}$R$_{13}$ the residues $R_{12}$ and $R_{13}$ may be the same or different or may form a ring. The ring may be further ring annelated by an aliphatic or aromatic ring. An example for that is:

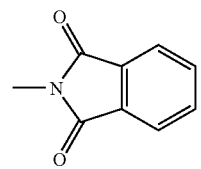

Examples for —N(R$_{12}$R$_{13}$), forming a 5- or 6-membered O-, S- or N-containing heterocyclic rings are:

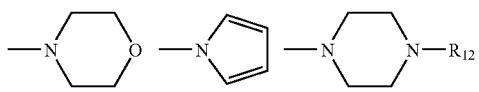

with R$_{12}$ as defined above.

Examples of —O-, S- or N-containing 5- or 6-membered heterocyclic rings are furyl, thienyl, pyrrolyl, oxinyl, dioxinyl or pyridyl. The cited heterocyclic radicals may be substituted by one to five, e.g. by one or two, linear or branched C$_1$-C$_8$alkyl, halogen and/or C$_1$-C$_8$alkoxy. Examples of such compounds are dimethylpyridyl, dimethylpyrrolyl or methylfuryl.

Substituted phenyl, naphthyl or biphenyl is substituted by one to five, e.g. by one, two, three or four, preferably by one, two or three, for example linear or branched C$_1$-C$_8$alkyl, linear or branched C$_1$-C$_8$alkoxy or by halogen.

Preferred substituents for phenyl, naphthyl and biphenyl are C$_1$-C$_4$alkyl, e.g. methyl, C$_1$-C$_4$alkoxy, e.g. methoxy or ethoxy, and chloro. Particularly preferred substituents are, for example, 2,4,6-trimethylphenyl, 2,6-dichlorophenyl, 2,6-dimethylphenyl or 2,6-dimethoxy-phenyl, 2-ethoxynapht-1-yl, 2-methylnaphth-1-yl.

R$_2$ is, for example, C$_1$-C$_{18}$alkyl or phenyl, preferably 2,4,6-trimethylphenyl, 2,6-dimethylphenyl or 2,6-dimethoxyphenyl, tert-butyl, 1,1-diphenylethyl, 2-phenylpropyl, 2-methylbutyl, 2-methylpentyl, most preferably 2,4,6-trimethylphenyl.

The residue of an alcohol is a group RO wherein R is C$_1$-C$_6$ branched or linear, alkyl, alkenyl, benzyl. R is, for example, ethyl, iso-propyl, n-propyl, t-butyl or n-butyl, 2-ethyl hexyl or other branched octyl species such as 2,4,4-trimethyloctyl.

The compound of formula I, wherein R$_1$ is —CO-phenyl which is substituted by one or more —CH$_3$, —OCH$_3$, —Cl is a triacylphosphane. These triacylphosphanes are preferably ortho-mono substituted.

The reducing metal (=Me) is selected from the group consisting of lithium, potassium, sodium, magnesium in combination with lithium preferably lithium, potassium, sodium, more preferably lithium or sodium, most preferably sodium.

MePH$_2$ may have the form of a cluster as shown in Example 11.

The common forms of elemental phosphorous (=[P]$_\infty$) include the white phosphorous, the red phosphorous which is high melting and less reactive than the white phosphorous, and the black phosphorous which is even less reactive. For the purposes of the process of this invention, the red phosphorous is preferred.

Other sources of reducible phosphorous are also suitable for use in this process. Suitable phosphorous compounds are those in which the formal oxidation state of the phosphorous atom is higher than (−3). Examples are phosphorous oxides such as P$_4$O$_n$ (n=6-10), (P$_2$O$_5$)$_o$ (o=1-∞), phosphorous trihalides PX$_3$ (X=halogen), including phosphorous trifluoride, phosphorous trichloride, phosphorous tribromide or phosphorous triiodide; phosphorous sulfides P$_4$S$_p$ (P=2-10) and (PS)$_q$ (q=0.25-8); phosphorous oxohalides or thiohalides such as POX$_3$. and PSX$_3$ (X=halogen); mixtures of the before mentioned compounds with metal oxides (Me$_k$H$_l$P$_m$O$_n$ phosphates, phosphonates, phosphinates), metal sulfides or metal halides, preferentially phosphorous containing minerals. Further useful phosphorous compounds are phosphazanes (R$_2$PNR$_2$), phosphazenes ((RPNR)$_x$, (R$_2$PN)$_x$, R$_3$PNR)) and phosphonitrides (PN or P$_3$N$_5$), as well as mixtures of these compounds with the reducible phosphorous compound mentioned before. Still another class of useful phosphorous compounds are phosphates (P=O(OR)$_3$); phosphonates (RP=O(OR)$_2$) and phosphites (R$_2$P=O(OR)), thiophosphates (P=S(OR)$_3$); thiophosphonates (RP=S(OR)$_2$) and thiophosphites (R$_2$P=S(OR)), with R being any organic radical.

For the purpose of the process of the invention, phosphorous trichloride is preferred. Useful catalysts in step a) and b) are aromatic polycyclic hydrocarbon catalysts, with or without heteroatoms, such as naphthalene, anthracene, phenanthrene, biphenyl, terphenyl, quaterphenyl, triphenylene, trans-1,2-diphenylethane, pyrene, perylene, acenapthalene, decacyclene, quinoline, N-ethylcarbazole, dibenzothiophene or dibenzofuran. It is preferred that a catalyst is present, which is preferably naphthalene and biphenyl, most preferably napththalene.

Other catalysts in step a) and b) are alkali or earth alkali hydroxides or Na, K, or Li alcoholates or alcohols.

Other catalysts in step a) and b) are combinations of alkali and/or earth alkali metals and/or alcohols.

Activators in step a) and b) are amines (triethylamine, tributylamine, piperidine, morpholine, N-methylpiperidine, N-methyl morpholine) or polyamines such as, for example TMEDA=N,N,N',N'-tetramethylethylenediamine, PMDTA=pentamethyldiethylenetriamine, or sparteine.

Other activators in step a) and b) are polyethers, such as crown ethers, for example 12-crown-6.

As solvent there are used ethers such as dimethyl ether, diethyl ether, methylpropyl ether, 1,2-dimethoxyethane (DME), bis(2-methoxyethyl)ether (diglyme), dioxane, or tetrahydrofuran, or in mixtures thereof, or arene solvents such as benzene, toluene, o-, m- or p-xylene, mesitylene, ethylbenzene, diphenylethane, 1,2,3,4-tetrahydronaphthalene (tetraline), iso-propylbenzene (cumol), or in mixtures thereof. Preferred solvents are ethers or mixtures of ethers and arene solvents, most preferred are ethers.

A suitable solvent for step a) and b) is liquid ammonia, a mixture of liquid ammonia and an ether such as tetrahydrofuran, a mixture of liquid ammonia and a tertiary alcohol or a tertiary alcohol alone.

Preferred is liquid ammonia and tetrahydrofuran.

The proton source is a CH-, NH-, SH-, or OH-acid compound.

CH-acid compounds have an active methylene group, such as, for example, malonic esters, cyanoacetic esters, acetylacetone, acetoacetic esters, succinic acid esters, N-methylpyrrolidone and the like. Furthermore an enol, an enol ether may be a CH-acid compound.

NH-acid compounds are, for example, lactams or pyrrolidone or salts such as ammonium salts or amidinium salts.

OH-acid, SH-acid compounds are alcohols or thioalcohols.

Preferred the proton source are sterically hindered alcohols, trialkylamine hydrohalogenes, bisarylamines, malono nitrile, malonic acid esters, amidine hydrohalogene R—C(=NH)—NH$_2$HCl and carboxylic acids.

The sterically hindered alcohol is selected from the group consisting of secondary or tertiary C$_3$-C$_{18}$alcohols, preferably of tert-butanol, tert-amyl-alcohol, 3-methyl-3-pentanol, 3-ethyl-3-pentanol, triphenylmethanol, 3,7-dimethyl-3-octanol, 2-methyl-1-phenyl-2-propanol, 2-methyl-4-phenyl-2-butanol, fenchyl alcohol, 2,4-dimethyl-3-pentanol, 1-dimethylamino-2-propanol or hexylene glycol, especially preferred tert-butanol, tert-amylalcohol or 3-methyl-3-pentanol.

The trialkylamine hydrohalogene is selected from tert-(C$_1$-C$_8$)$_3$N—HCl, preferably trimethyl-amine hydrochloride, triethylamine hydrochloride or tributylamine hydrochloride.

Preferred Substituents:

In the above-described processes m=2 is preferred and $R_1$, if n=1, is phenyl or unsubstituted linear or branched $C_1$-$C_{18}$alkyl or $C_2$-$C_{18}$alkenyl; or linear or branched $C_1$-$C_{18}$alkyl or $C_2$-$C_{18}$alkenyl substituted once or more than once by groups selected from:

halogen or CN, or

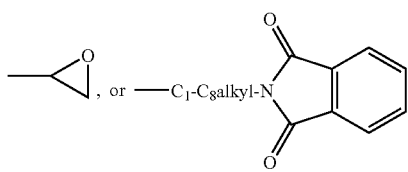

—$OR_{10}$, —$SR_{10}$, —OCO—$R_{10}$, —COO—$R_{10}$, —CH=CH—CO—$OR_{10}$ or

—C($C_1$-$C_4$alkyl)=C($C_1$-$C_4$alkyl)-CO—$OR_{10}$; wherein $R_{10}$ is hydrogen, $C_1$-$C_{18}$alkyl, or $C_2$-$C_{18}$alkyl which is interrupted by one or several non-successive —O-atoms, a di, -tri, -tetra- or polyethylene glycol residue, $C_3$-$C_{12}$-cycloalkyl, tetrahydropyran-2-yl, phenyl-$C_1$-$C_4$-alkylene, phenyl-$C_1$-$C_4$-alkenylene, $C_1$-$C_6$alkyl substituted by halogen or substituted by cyclohexyl or cyclopentyl, or substituted by tetrahydrofuranyl, furanyl, isopropyl-4-methyl-cyclohexyl, $C_2$-$C_{18}$-alkenyl, unsubstituted phenyl, naphthyl or biphenyl being unsubstituted or phenyl, naphthyl or biphenyl substituted by one to five $C_1$-$C_8$-alkyl, $C_1$-$C_8$-alkoxy, $C_1$-$C_8$-alkylthio and/or halogen; and $R_2$ is phenyl or phenyl which is substituted by halogen, $C_1$-$C_4$alkoxy or $C_1$-$C_4$alkyl.

Especially preferred are n=1 and $R_1$ is phenyl linear or branched $C_1$-$C_8$alkyl or $C_2$-$C_{18}$alkenyl or is linear or branched $C_1$-$C_8$alkyl or $C_2$-$C_{18}$alkenyl substituted by CN, trifluormethyl, oxiranyl, isoindole-1,3-dione, —O—$C_1$-$C_{18}$alkyl, —O-benzyl, —CO-phenyl, —CO—$C_1$-$C_{18}$alkyl, —OCO—$C_1$-$C_{18}$alkyl; —OCO—$C_1$-$C_{18}$alkenyl; —COO—$C_1$-$C_{18}$alkyl; —COO—$C_1$-$C_{18}$alkylene-phenyl, —COO—$C_1$-$C_{18}$alkylene-cycloalkyl, —COO—$C_1$-$C_{18}$alkylene-tetrahydrofuranyl, —COO—$C_1$-$C_{18}$alkylene-furanyl, —COO-cycloalkyl, —COO—$C_1$-$C_{18}$alkenyl; —COO—$C_1$-$C_{18}$alkenylene-phenyl; —COO—($CH_2$)$_{2-3}$—Cl, —COO—[($CH_2$)$_{2-3}$—O]$_{1-10}$—$C_1$-$C_6$alkyl; —COO—[($CH_2$)$_{2-3}$—O]$_{1-10}$—$C_1$-$C_6$—OH, —CO—$CH_2$—CO—$C_1$-$C_{18}$alkyl; —CO—$CH_2$—COO—$C_1$-$C_{18}$alkyl, —O-tetrahydropyranyl, bicyclo[2.2.1]hept-2-en-5-yl)-methyl, PO(O$C_1$-$C_6$alkyl)$_2$ and wherein $R_2$ is phenyl which is substituted in 2,6- or 2,4,6-position by $C_1$-$C_4$alkyl and/or $C_1$-$C_4$alkoxy, and/or chlorine; 2-ethoxy-naphth-1-yl, 2-methyl-naphth-1-yl or anthr-9-yl.

Especially preferred for n=2 $R_1$, if n=2, is $C_6$-$C_{10}$alkylene, or biphenylene or —$CH_2$—COO-Z-OCO—$CH_2$— wherein Z is $C_1$-$C_{18}$ alkylene or a bridge derived from a di, -tri, -tetra- or polyethylene glycol.

$R_3$ is $C_1$-$C_{12}$alkyl, cyclohexyl, phenyl or biphenyl, the radicals phenyl and biphenyl being unsubstituted or substituted by one to four $C_1$-$C_8$alkyl and/or $C_1$-$C_8$alkoxy.

Compounds of formula I which are particularly preferably used in the above process are those wherein n is 1.

The residue "Hal" is preferably chloro.

Other preferred compounds of formula I in the above process are those, wherein m is defined as the number two, i.e. bisacylphosphane or bisacylphosphane oxides or bisacylphosphane sulfides.

The process is especially suitable to prepare alkyl bisacylphosphanes ($R_1$ is unsubstituted or substituted $C_1$-$C_{18}$alkyl).

Using the inventive process it is possible to prepare new (bis)acylphosphanes which are also part of the invention.

Thus the invention relates to acylphosphanes and bisacylphosphanes of the formula I

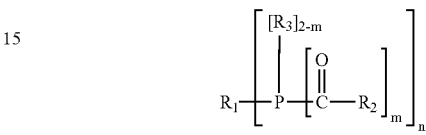

wherein n=1 and $R_1$ is linear or branched $C_1$-$C_8$alkyl or $C_2$-$C_{18}$alkenyl substituted by CN, trifluormethyl, oxiranyl, isoindole-1,3-dione, —O—$C_1$-$C_{18}$alkyl, —O-benzyl, —CO-phenyl, —CO—$C_1$-$C_{18}$alkyl, —OCO—$C_1$-$C_{18}$alkyl; —OCO—$C_1$-$C_{18}$alkenyl; —COO—$C_1$-$C_{18}$alkyl; —COO—$C_1$-$C_{18}$alkylene-phenyl, —COO—$C_1$-$C_{18}$alkylene-cycloalkyl, —COO—$C_1$-$C_{18}$alkylene-tetrahydrofuranyl, —COO—$C_1$-$C_{18}$alkylene-furanyl, —COO-cycloalkyl, —COO—$C_1$-$C_{18}$alkenyl; —COO—$C_1$-$C_{18}$alkenylene-phenyl; —COO—($CH_2$)$_{2-3}$—Cl, —COO—[($CH_2$)$_{2-3}$—O]$_{1-10}$—$C_1$-$C_6$alkyl; —COO—[($CH_2$)$_{2-3}$—O]$_{1-10}$—$C_1$-$C_6$—OH, —CO—$CH_2$—CO—$C_1$-$C_{18}$alkyl; —CO—$CH_2$—COO—$C_1$-$C_{18}$alkyl, —O-tetrahydropyranyl, bicyclo[2.2.1]hept-2-en-5-yl)-methyl, PO(O$C_1$-$C_6$alkyl)$_2$ and wherein m $R_2$ and $R_3$ are as defined in claim 1.

Process Parameters

Step a)

The elemental phosphorous may be employed as a finely divided solid or as a melt, or it may be dissolved or dispersed in an inert organic solvent. As elemental phosphorous is spontaneously flammable in moist air, it is preferred that the reaction be carried out in an inert gas atmosphere.

$PCl_3$ is preferentially dissolved in an inert organic solvent; Other suitable phosphorous compounds with a formal oxidation state of the phosphorous atom higher than −3 are employed as solids, in suspension or dissolved in an inert organic solvent.

As solvents, ethers such as dimethoxyethane, liquid ammonia or a mixture of liquid ammonia and tetrahydrofuran are preferred.

Step a) is preferably carried out in the presence of a hydrocarbon catalyst.

Advantageously, the reaction of the reducing metal, dispersed in a solvent, and phosphorous may be effected at temperatures ranging from −70° C. to +160° C., e.g. from room temperature to 80° C.

Step b)

In the inventive process step b) is optionally. Thus, metal phosphides $Me_nP_m$ [e.g. trialkali metal phosphide ($Me_3P$)] may react directly with the acylating agent. However, because of an improved yield, step b) is preferably carried out. The reaction temperature is preferably in the range from −20° C. to +160° C., e.g. from room temperature to 80° C.

Catalysts and activators in step a) and b) are used in a molar ratio of catalyst to the reducing metal of for example 1:2 to 1:1000.

Catalysts and activators in step a) and b) may be added prior or during the reduction of elemental phosphorous.

It is possible to optionally isolate the product of step b) as an alcoholate cluster of the phosphide before using it in step c).

It is possible to add polar or dipolar co-solvents to the reaction mixture during or after step a) and b). Such solvents may be linear or cyclic amides like dimethylacetamide (DMA), n-methyl pyrrolidone (NMP), cyclic ureas like 1,3-dimethylpropylene urea (DMPU), linear and cyclic glycols like diglyme and dimethoxyethane (DME).

Step c)

The reaction temperature for the reaction with the acid halide is usefully in the range from −20° to +80° C. A bisa-cylphosphide intermediate is formed which may form an O-coordinated bisacylphosphaenolate chelate complex of the formula (V') or (Va')

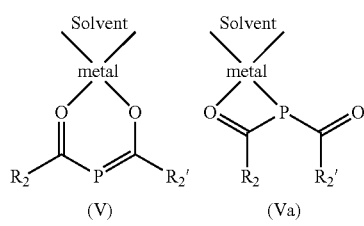

(V)    (Va)

The bisacylphosphide intermediate is stabilized due to the formation of an O-coordinated bisacylphosphaenolate chelate complex in the case of alkali metals. The complex might be further stabilized by metal-metal exchange. Suitable exchange metals are: boron, aluminium, chromium, nickel.

Step d)

The enolate may be isolated or may easily be further reacted with an electrophilic agent. The choice of the electrophilic agent is not limited. Non limiting examples are: straight-chain or branched $C_1$-$C_{18}$alkyl halides, $C_2$-$C_8$alkenyl halides, substituted alkylhalides such as fluoro, or hydroxy, or carbonyl, or sulfonyl, or vinyl, or siloxanyl, or alkoxycarbonyl, or acyloxy or by heterocyclic groups substituted alkylhalides, $C_5$-$C_{12}$cycloalkyl halides, benzyl halides and aryl halides such as phenyl halide, naphthyl halide or biphenyl halide. Other electophilic agents are alkyl sulfates, alkyltosylates, alkylmethylsulfonates, epoxides, episulfide or acrylate or methacrylate esters. It is likewise possible to use alkylating reagents giving ionic functions, e.g., monobromoacetic acid, monobromopropionic acid, sodium 3-bromopropanesulfonate and N-(2-bromoethyl)diethylamine. Silyl or siloxanyl groups may be implemented via chlorosilane or chlorosiloxane, or by the use of α-halo-ω-silanyl or siloxanylalkanes.

The reaction temperature in step d) is usefully in the range from room temperature to 100°.

The bisacylphosphane of formula I can be isolated by the customary technological methods which are known to the skilled person, for example by filtration, evaporation or distillation. Likewise, the customary methods of purification may be used, for example crystallisation, distillation or chromatography.

However, the phosphanes can also be reacted without isolation to the corresponding mono- or bisacylphosphane oxides or mono- or bisacylphosphane sulfides.

Using the process of this invention it is also possible to prepare mono- and bisacylphosphanes together in one reaction step.

Depending on the substituents used, unsymmetric compounds may be formed by the novel process.

Monoacylphosphane oxides are compounds of the formula I' corresponding to compounds of the formula I wherein n=1 and m=1.

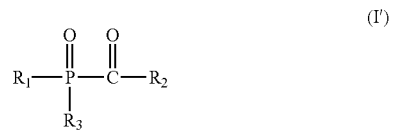

The residues $R_1$ and $R_3$ may be the same or may be different.

Bisacylphosphane oxides are compounds of the formula I''' corresponding to compounds of the formula I wherein n=1 and m=2.

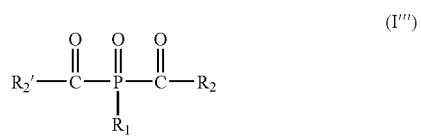

The residues $R_2$ and $R_2'$ may be the same or may be different.

By means of the novel process it is furthermore also possible to prepare mixtures of aliphatic and aromatic monoacylphosphanes or mixtures of aliphatic and aromatic bisacylphosphanes.

If required, all of the mixtures may be separated by the processes customarily used in the technology or they may be further used as they are.

This invention also relates to a process for the preparation of mono- and bisacylphosphane oxides or mono- and bisacylphosphane sulfides. This process is first carried out as described above and a mono- or bisacylphosphane (I) is prepared. The crude reaction product (I) can then be further processed without purification and an additional reaction step may be carried out without isolation of the phosphane (I) using the solution of the crude product. If required, the solvent may be changed, for example, by concentrating the solution containing the mono- or bisacylphosphane and taking up the residue in a new solvent. Of course it is also possible to further react above-described unseparated mixtures of compounds of formula (I) to the corresponding oxide or sulfide.

It is recommended to adjust the pH of the reaction mixture prior to the oxidation step to a pH of 2-8, preferably to a pH of 3-6 by addition of typical inorganic and/or organic acids or buffer systems.

When preparing the respective oxide (VIa), the oxidation of the phosphane (I) is carried out using the oxidant conventionally used in the technology

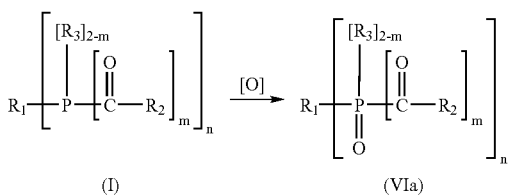

Suitable oxidants are in particular hydrogen peroxide and organic peroxy compounds, for example peracetic acid or t-butylhydroperoxide, air or pure oxygen.

The oxidation is usefully carried out in solution. Suitable solvents are aromatic hydrocarbons, such as benzene, toluene, m-xylene, p-xylene, ethylbenzene or mesitylene, or aliphatic hydrocarbons, such as alkanes and alkane mixtures, e.g. petroleum ether, hexane or cyclo-hexane. During oxidation, the reaction temperature is preferably kept in the range from 0° to 120° C., preferably from 20° and 80° C.

The reaction products (VIa) can be isolated and purified by conventional processing methods known to the skilled person.

The respective sulfide (VIb) is prepared by reaction with sulfur:

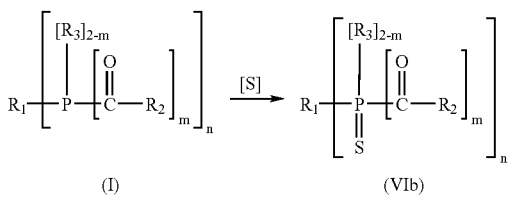

The mono- or bisacylphosphanes (I) are in this case reacted in substance or, where appropriate, in a suitable inert organic solvent with an equimolar to 2-fold molar amount of elementary sulfur. Suitable solvents are for example those described for the oxidation reaction. However, it is also possible to use e.g. aliphatic or aromatic ethers, such as dibutyl ether, dioxane, diethylene glycol dimethyl ether or diphenyl ether, in the temperature range from 20° to 250° C., preferably from 60° to 120° C. The resulting mono- or bisacylphosphane sulfide, or its solution, is usefully freed from any remaining elementary sulfur by filtration. After the solvent is removed, the mono- or bisacylphosphane sulfide can be isolated by distillation, chromatography or recrystallisation in pure form.

As mentioned above, it is also possible to use mixtures of compounds of formula I for the oxidation or reaction to the sulfide. The correspondingly obtained oxide or sulfide mixtures can either be separated by processes customarily used in the technology or may be used as mixtures.

All of the above reactions are usefully carried out with exclusion of air in an inert gas atmosphere, e.g. under nitrogen or argon gas. The respective reaction mixture is usefully also stirred.

The acid halides (III, III'), the carboxylic acid esters (IV, IV') or the electrophilic compounds $R_1$-Hal or $R_3$-Hal used as starting materials are known substances, some of which are commercially available, or may be prepared in analogy to known compounds.

It is characteristic of the novel process that the individual processing steps can be carried out directly one after the other without the need for isolating and purifying the respective intermediates.

Mixtures such as those described in the process for the preparation of the corresponding phosphanes may also be formed, or may also be specifically produced, in the above-described process for the preparation of mono- or bisacylphosphane oxides or mono- or bis-acylphosphane sulfides. Such mixtures can be separated by methods known in the technology or may be further used in the form of mixtures.

The phosphanes which are accessible by the novel process are important educts for the preparation of the corresponding phosphane oxides and phosphane sulfides. The phosphane oxides and phosphane sulfides are used in the art as initiators in photopolymerisation reactions.

The oxidation is usefully carried out in solution. Suitable solvents are aromatic hydrocarbons, such as benzene, toluene, m-xylene, p-xylene, ethylbenzene or mesitylene, or aliphatic hydrocarbons, such as alkanes and alkane mixtures, e.g. petroleum ether, hexane or cyclo-hexane. During oxidation, the reaction temperature is preferably kept in the range from 0° to 120° C., preferably from 20° and 80° C. The reaction products can be isolated and purified by conventional processing methods known to the skilled person.

Using the process of this invention it is possible to prepare bisacylphosphanes or bisacylphospane oxides or sulfides without isolating any intermediate ("one-pot" reaction).

If two different acid halides or two different carboxylic acid esters are used, unsymmetric compounds may be formed by the novel process. Preferred is a process wherein a carboxylic acid ester followed by an acid chloride of a different acid may be used for the synthesis of unsymmetric compounds.

The phosphanes which are accessible by the novel process are important educts for the preparation of the corresponding phosphane oxides and phosphane sulfides. The phosphane oxides and phosphane sulfides are used in the art as initiators in photopolymerisation reactions.

Preferences

A process for the preparation of (bis)acylphosphanes or (bis)acylphosphane oxides of formula I or VI the process comprising the steps of:

a) contacting red phosphorous or $PCl_3$ with an alkali metal in the presence of a solvent and optionally in the presence of polycyclic hydrocarbon catalyst b) adding a sterically hindered alcohol;

c) subsequent reaction with two equivalents of an acid halide Hal-CO—$R_2$ to obtain a metal bisacylphosphide [$R_2$—CO—P=C(OMe)$R_2$], wherein Me is Na or Li; or with one equivalent of a carboxylic acid ester RO—CO—$R_2$, followed by one equivalent of an acid halide Hal-CO—$R_2$' to obtain a metal bisacylphosphide [$R_2$—CO—P=C(OMe)$R_2$'], wherein Me is an alkali metal d) subsequent reaction with an electrophilic agent $R_1$Hal or $R_1OSO_2OR_1$ to obtain the compounds of formula I.

Preferred is a step a) whereby sodium in liquid ammonia is contacted with red phosphorus in tetrahydrofuran.

The following examples illustrate the invention in more detail, although it is not intended that the invention be limited to the examples. As in the remaining description and in the patent claims, parts or percentages are by weight, unless otherwise stated.

EXAMPLES
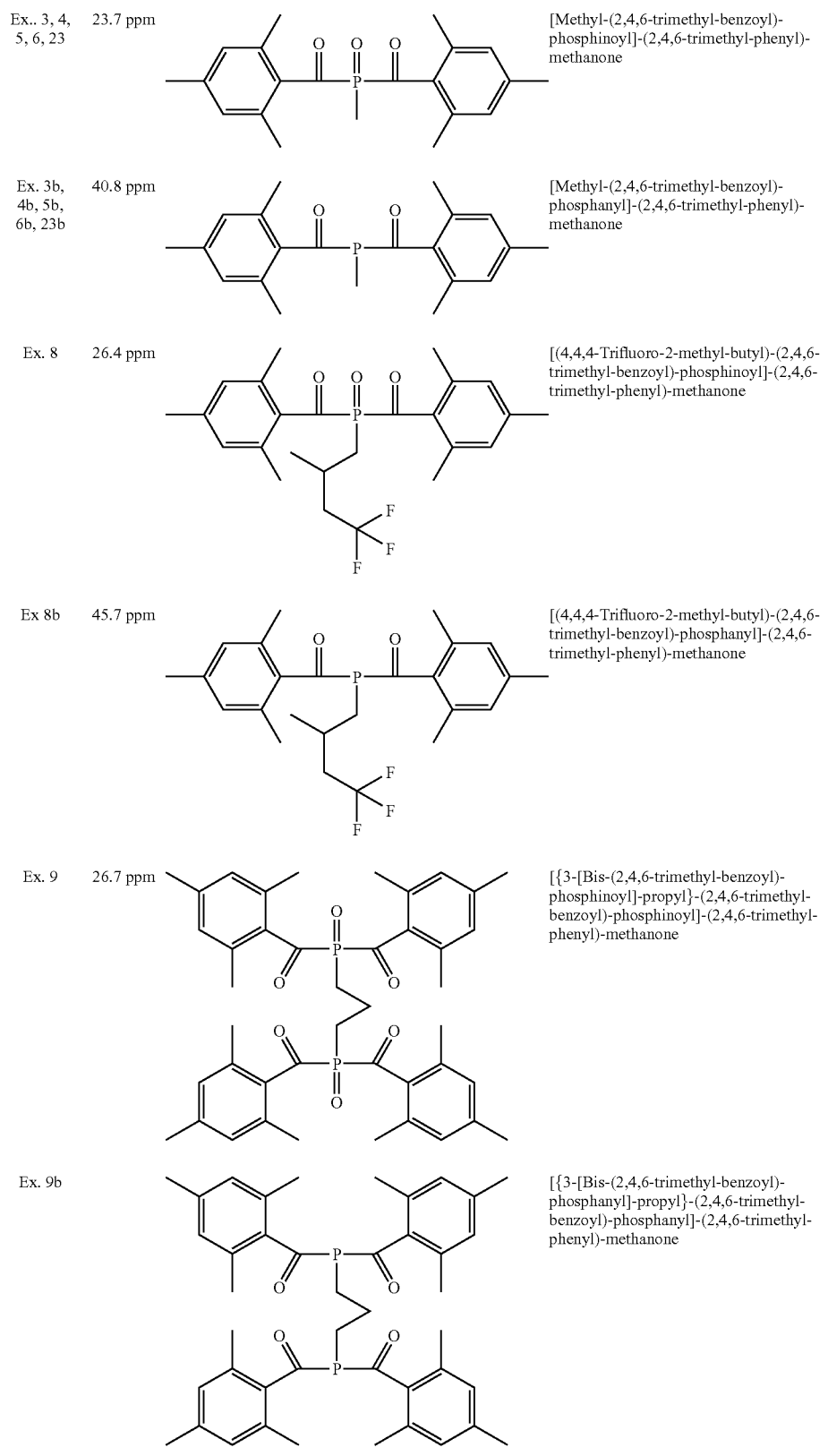

Novel compounds

| Ex. | $^{31}$P-NMR | Struktur | IUPAC-Namen |
|---|---|---|---|
| 14 | 28.2 ppm | | 2,2-Dimethyl-1-[methyl-(2,4,6-trimethyl-benzoyl)-phosphinoyl]-propan-1-one |
| 14b | 23.7 ppm | | 2,2-Dimethyl-1-[methyl-(2,4,6-trimethyl-benzoyl)-phosphanyl]-propan-1-one |
| 15 | 27.5 ppm | | Acetic acid 3-[bis-(2,4,6-trimethyl-benzoyl)-phosphinoyl]-propyl ester |
| 15b | 53.2 ppm | | Acetic acid 3-[bis-(2,4,6-trimethyl-benzoyl)-phosphanyl]-propyl ester |
| 16 | 29.0 ppm | | Acetic acid 6-[bis-(2,4,6-trimethyl-benzoyl)-phosphinoyl]-hexyl ester |

-continued

Novel compounds

| Ex. | 31P-NMR | Struktur | IUPAC-Namen |
|---|---|---|---|
| 16b | 53.5 ppm | | Acetic acid 6-[bis-(2,4,6-trimethyl-benzoyl)-phosphanyl]-hexyl ester |
| 17 | 18.1 ppm | | [Bis-(2,4,6-trimethyl-benzoyl)-phosphinoyl]-acetic acid methyl ester |
| 17b | 47.7 ppm | | [Bis-(2,4,6-trimethyl-benzoyl)-phosphanyl]-acetic acid methyl ester |
| 18 | 18.4 ppm | | [Bis-(2,4,6-trimethyl-benzoyl)-phosphinoyl]-acetic acid ethyl ester |
| 19 | 25.4 ppm | | 2-[Bis-(2,4,6-trimethyl-benzoyl)-phosphinoyl]-propionic acid ethyl ester |

-continued
Novel compounds
| Ex. | 31P-NMR | Struktur | IUPAC-Namen |
|---|---|---|---|
| 19b | 74.18 ppm | 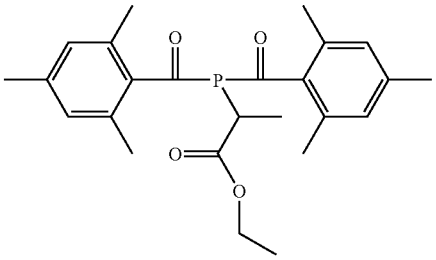 | 2-[Bis-(2,4,6-trimethyl-benzoyl)-phosphanyl]-propionic acid ethyl ester |
| 20 | 19.4 ppm | 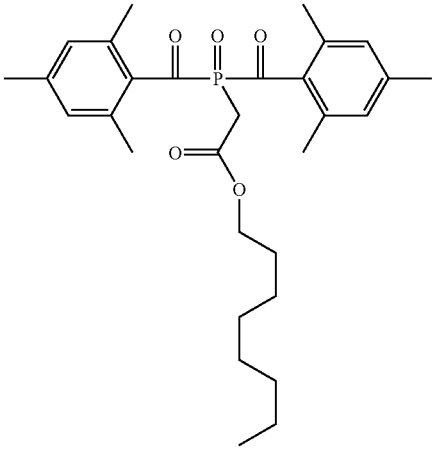 | [Bis-(2,4,6-trimethyl-benzoyl)-phosphinoyl]-acetic acid octyl ester |
| 20b | 47.6 ppm | 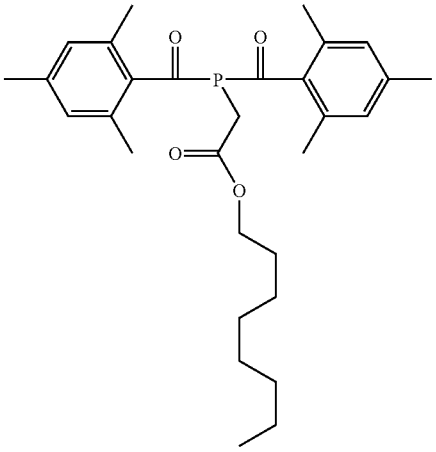 | [Bis-(2,4,6-trimethyl-benzoyl)-phosphanyl]-acetic acid octyl ester |
| 21 | 19.1 ppm | 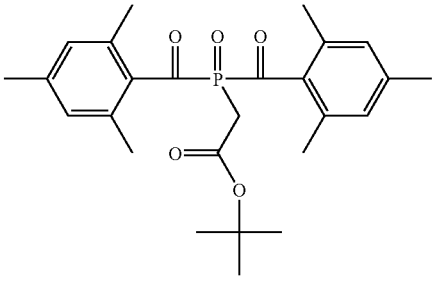 | [Bis-(2,4,6-trimethyl-benzoyl)-phosphinoyl]-acetic acid tert-butyl ester |

-continued

Novel compounds

| Ex. | 31P-NMR | Struktur | IUPAC-Namen |
|---|---|---|---|
| 21b | 46.3 ppm | 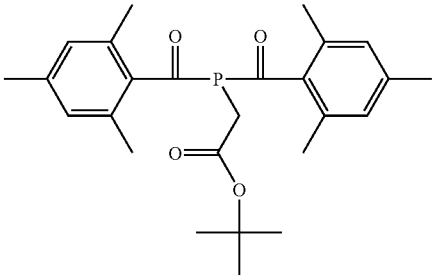 | [Bis-(2,4,6-trimethyl-benzoyl)-phosphanyl]-acetic acid #tert!-butyl ester |
| 22 | 18.4 ppm | 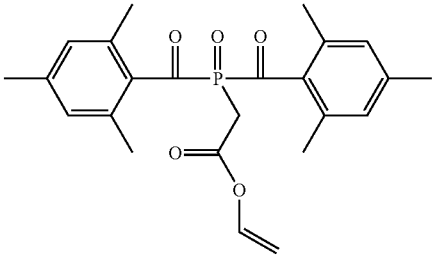 | [Bis-(2,4,6-trimethyl-benzoyl)-phosphinoyl]-acetic acid vinyl ester |
| 22b | 47.9 ppm | 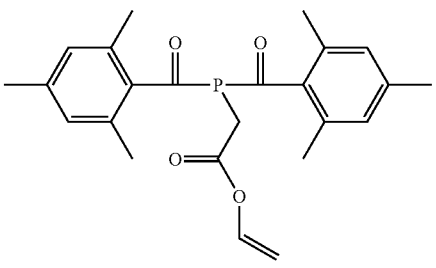 | [Bis-(2,4,6-trimethyl-benzoyl)-phosphanyl]-acetic acid vinyl ester |
| 23 | 23.7 ppm | 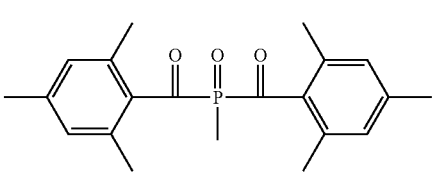 | [Methyl-(2,4,6-trimethyl-benzoyl)-phosphinoyl]-(2,4,6-trimethyl-phenyl)-methanone |
| 23b | 40.8 ppm | 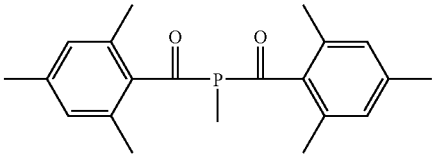 | [Methyl-(2,4,6-trimethyl-benzoyl)-phosphanyl]-(2,4,6-trimethyl-phenyl)-methanone |
| 24 | 27.9 ppm | 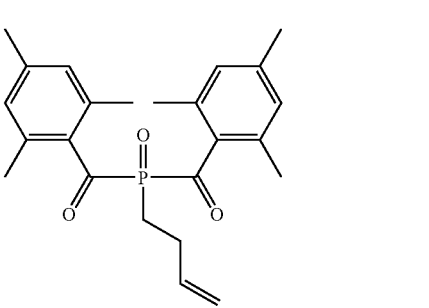 | [But-3-enyl-(2,4,6-trimethyl-benzoyl)-phosphinoyl]-(2,4,6-trimethyl-phenyl)-methanone |

-continued

Novel compounds

| Ex. | 31P-NMR | Struktur | IUPAC-Namen |
|---|---|---|---|
| 24b | 52.5 ppm | | [But-3-enyl-(2,4,6-trimethyl-benzoyl)-phosphanyl]-(2,4,6-trimethyl-phenyl)-methanone |
| 25 | 21.7 ppm | | 3-[Bis-(2,4,6-trimethyl-benzoyl)-phosphinoyl]-propionitrile |
| 25b | 51.6 ppm | | 3-[Bis-(2,4,6-trimethyl-benzoyl)-phosphanyl]-propionitrile |
| 26 | 25.5 ppm | | [(2-Benzyloxy-ethyl)-(2,4,6-trimethyl-benzoyl)-phosphinoyl]-(2,4,6-trimethyl-phenyl)-methanone |
| 26b | 46.0 ppm | | [(2-Benzyloxy-ethyl)-(2,4,6-trimethyl-benzoyl)-phosphanyl]-(2,4,6-trimethyl-phenyl)-methanone |

-continued

Novel compounds

| Ex. | 31P-NMR | Struktur | IUPAC-Namen |
|---|---|---|---|
| 27 | 25.1 ppm | | [[2-(Tetrahydro-pyran-2-yloxy)-ethyl]-(2,4,6-trimethyl-benzoyl)-phosphinoyl]-(2,4,6-trimethyl-phenyl)-methanone |
| 27b | 46.1 ppm | | [[2-(Tetrahydro-pyran-2-yloxy)-ethyl]-(2,4,6-trimethyl-benzoyl)-phosphanyl]-(2,4,6-trimethyl-phenyl)-methanone |
| 28 | 24.4 ppm | | 2-Methyl-acrylic acid 2-[bis-(2,4,6-trimethyl-benzoyl)-phosphinoyl]-ethyl ester |
| 28b | 47.1 ppm | | 2-Methyl-acrylic acid 2-[bis-(2,4,6-trimethyl-benzoyl)-phosphanyl]-ethyl ester |
| 29 | 22.1 ppm | | [Oxiranylmethyl-(2,4,6-trimethyl-benzoyl)-phosphinoyl]-(2,4,6-trimethyl-phenyl)-methanone |

-continued

Novel compounds

| Ex. | $^{31}$P-NMR | Struktur | IUPAC-Namen |
|---|---|---|---|
| 29b | 47.4 ppm | | [Oxiranylmethyl-(2,4,6-trimethyl-benzoyl)-phosphanyl]-(2,4,6-trimethyl-phenyl)-methanone |
| 30 | 13.2 ppm | | 2-[Bis-(2,4,6-trimethyl-benzoyl)-phosphinoylmethyl]-isoindole-1,3-dione |
| 30b | 45.3 ppm | | 2-{[Bis-(2,4,6-trimethyl-benzoyl)-phosphanyl]-methyl}-isoindole-1,3-dione |
| 31 | 21.0 ppm | | 2-[Bis-(2,4,6-trimethyl-benzoyl)-phosphinoyl]-1-phenyl-ethanone |
| 31b | 46.7 ppm | | 2-[Bis-(2,4,6-trimethyl-benzoyl)-phosphanyl]-1-phenyl-ethanone |

-continued

Novel compounds

| Ex. | $^{31}$P-NMR | Struktur | IUPAC-Namen |
|---|---|---|---|
| 32 | 47.1 ppm | | [Bis-(2,4,6-trimethyl-benzoyl)-phosphanyl]-acetic acid ethyl ester |
| 33 | 27.0 ppm | | Acetic acid 3-[bis-(2,6-dimethoxy-benzoyl)-phosphinoyl]-propyl ester |
| 33b | 55.4 ppm | | Acetic acid 3-[bis-(2,6-dimethoxy-benzoyl)-phosphanyl]-propyl ester |
| 34 | 17.9 ppm | | [Bis-(2,6-dimethoxy-benzoyl)-phosphinoyl]-acetic acid ethyl ester |
| 34b | 48.1 ppm | | [Bis-(2,6-dimethoxy-benzoyl)-phosphanyl]-acetic acid ethyl ester |

-continued

Novel compounds

| Ex. | ³¹P-NMR | Struktur | IUPAC-Namen |
|---|---|---|---|
| 35 | 20.0 ppm | | 3-[Bis-(2,6-dimethoxy-benzoyl)-phosphinoyl]-acetic acid tert-butyl ester |
| 35b | 48.38 ppm | | [Bis-(2,6-dimethoxy-benzoyl)-phosphanyl]-acetic acid tert-butyl ester |
| 36 | 26.2 ppm | | 3-[Bis-(2,6-dimethoxy-benzoyl)-phosphinoyl]-propionic acid tert-butyl ester |
| 36b | 53.6 ppm | | 3-[Bis-(2,6-dimethoxy-benzoyl)-phosphanyl]-propionic acid tert-butyl ester |

-continued

Novel compounds

| Ex. | $^{31}$P-NMR | Struktur | IUPAC-Namen |
|---|---|---|---|
| 37 | 25.0 ppm | | Acetic acid 3-[bis-(2,6-dichloro-benzoyl)-phosphinoyl]-propyl ester |
| 37b | 48.8 ppm | | Acetic acid 3-[bis-(2,6-dichloro-benzoyl)-phosphanyl]-propyl ester |
| 38 | 15.2 ppm | | [Bis-(2,6-dichloro-benzoyl)-phosphinoyl]-acetic acid ethyl ester |
| 38b | 37.9 ppm | | [Bis-(2,6-dichloro-benzoyl)-phosphanyl]-acetic acid ethyl ester |
| 39 | 28.8 d<br>24.5 d<br>(J = 60 Hz) | | {2-[Bis-(2,4,6-trimethyl-benzoyl)-phosphinoyl]-ethyl}-phosphonic acid diethyl ester |

-continued

Novel compounds

| Ex. | ³¹P-NMR | Struktur | IUPAC-Namen |
|---|---|---|---|
| 39b | 55.6 d<br>28.2 d,<br>(J = 54.7 Hz) | | {2-[Bis-(2,4,6-trimethyl-benzoyl)-phosphanyl]-ethyl}-phosphonic acid diethyl ester |
| 40 | 28.0/27.3 ppm (endo/exo) | | [Bicyclo[2.2.1]hept-5-en-2-ylmethyl-(2,4,6-trimethyl-benzoyl)-phosphinoyl]-(2,4,6-trimethyl-phenyl)-methanone |
| 40b | 50.4/49.9 ppm (endo/exo) | | [Bicyclo[2.2.1]hept-5-en-2-ylmethyl-(2,4,6-trimethyl-benzoyl)-phosphanyl]-(2,4,6-trimethyl-phenyl)-methanone |
| 41 | 17.81 | | [Bis-(2-ethoxy-naphthalene-1-carbonyl)-phosphinoyl]-acetic acid ethyl ester |
| 41a | 51.77 | | [Bis-(2-ethoxy-naphthalene-1-carbonyl)-phosphanyl]-acetic acid ethyl ester |

General: Solvents are used as received (without any treatment) or dried over molecular sieves or by azeotropic distillation. The course of the reaction is monitored by $^{31}$P-NMR spectroscopy.

Example 1

Preparation of [isobutyl-(2,4,6-trimethyl-benzoyl)-phosphinoyl]-(2,4,6-tri-methyl-phenyl)-methanone using sodium and tert-butanol as proton source

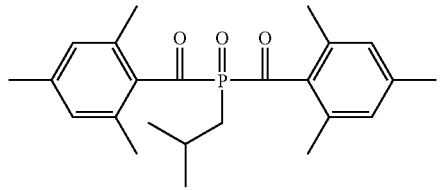

formula I $R_1$=iso-butyl, $R_2$=mesityl, m=2 a) Preparation of Na$_3$P 3.45 g of sodium sand (150 mmol, 3 eq., M=22.99 g/mol), 1.55 g of purified red phosphorous (50.0 mmol, 1 eq., M=30.97 g/mol) and 125 mg of naphthalene (1.0 mmol, M=128.17 g/mol) are suspended in 120 ml of dimethoxyethane (DME). The suspension is heated up to 75° C. and kept at this temperature for 20 h under stirring. A color change from green over red-brown into black takes place.

b) Preparation of NaPH$_2$

The reaction mixture of step a) is cooled down to −10 to −15° C. 10 ml of tert-butanol (0.1 mol, 2 eq., M=74.12 g/mol) in 10 ml DME is added within 20 min under stirring. A nearly clear brown solution is obtained, containing a small amount of unreacted sodium. Stirring is continued for another 20 min.

c) Preparation of sodium bis(mesitoyl)phosphide×DME, {Na[P(COMes)$_2$]×DME}

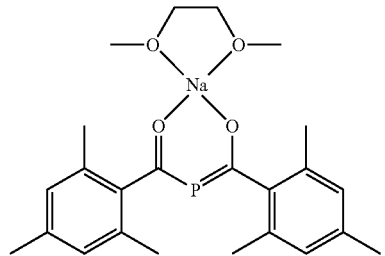

16.8 ml of 2,4,6-trimethylbenzoyl chloride (TMBCl) (0.1 mol, 2 eq., M=182.65 g/mol) are quickly added to the reaction mixture of step b), resulting in a color change to yellow. The reaction mixture is left stirring for another 20 min under ice cooling, followed by stirring for one hour at room temperature. The $^{31}$P NMR spectra shows a signal for sodium bis(mesitoyl)phosphide×DME {Na[P(COMes)$_2$]×DME} at 82 ppm (>95%).

c-1) Isolation of {Na[P(COMes)$_2$]×DME}

The reaction mixture of step c) is concentrated under high vacuum. The resulting orange-yellow foam is taken up in 100 ml of toluene and then filtered through G4/Celite. The filter cake is twice washed with toluene providing a clear orange-yellow filtrate solution. The filtrate solution is concentrated under vacuum to a volume of about 70 ml, and then carefully overlayed with hexane (30 ml). Yellow cubic crystals separate from the solution and are identified as sodium bis(mesitoyl) phosphide×DME {Na[P(COMes)$_2$]×DME} ($C_{24}H_{32}NaO_4P$, M=438.47 g/mol) by $^{31}$P-, $^1$H- and $^{13}$C-NMR spectroscopy. Furthermore, single-crystal X-ray structural analysis shows that the crystals are composed of an ion pair complex of the formula [Na$_3$[P(COMes)$_2$]$_4$][Na(DME)$_3$]. The yellow crystals are soluble in toluene, THF and DME, however little soluble in hexane.

M.p.=208° C. $^1$H-NMR (250.13 MHz, $C_6D_6$, 25° C.): δ=6.60 (s, 4H, Mes CH), 2.94 (s, 4H, DME CH$_2$), 2.87 (s, 6H, DME CH$_3$), 2.61 (s, 12H, Mes o-CH$_3$), 2.08 (s, 6H, Mes p-CH$_3$). $^{13}$C{H}-NMR (75.47 MHz, $C_6D_6$, 25° C.): δ=236.2 (d, $^1J_{CP}$=94.0 Hz, CO), 145.5 (d, $^2J_{CP}$=38.3 Hz, Mes $C^1$), 136.3 (d, $^5J_{CP}$=0.9 Hz, Mes $C^4$), 133.9 (d, $^3J_{CP}$=2.7 Hz, Mes $C^{2,6}$), 128.3 (s, Mes $C^{3,5}$), 71.0 (s, DME CH$_2$), 58.4 (s, DME CH$_3$), 21.1 (s, Mes p-CH$_3$), 20.1 (d, $^4J_{CP}$=2.5 Hz, Mes o-CH$_3$). $^{31}$P{H}-NMR (101.25 MHz, $C_6D_6$, 25° C.): δ=84.1 (br.).

c-2) A DME-free product is obtained if the toluene filtrate solution from step c-1) is completely concentrated under vacuum first. The residue is suspended in n-hexane (80 ml), the resulting yellow solid filtered off and then dried under high vacuum. According to NMR spectroscopy measurements, the product consists of DME-free {Na[P(COMes)$_2$]} ($C_{20}H_{22}NaO_2P$, M=348.35 g/mol).

d) Alkylation to iso-BuP(COMes)$_2$

The solution obtained in step c) is concentrated to 80 ml. 9.6 g of isobutyl bromide (0.07 mol, 1.4 eq., M=137.02 g/mol) are added. The yellow-orange suspension is heated up to 60° C. and kept at this temperature for 96 h under stirring. The $^{31}$P NMR spectra of the reaction solution shows a signal for iso-BuP(COMes)$_2$ at 48 ppm (>91%). The light-yellow suspension is filtered through G4/Celite and the filter cake washed once with DME (10 ml). All volatile compounds are removed under high vacuum giving iso-BuP(COMes)$_2$ as a yellow oil.

e) Oxidation to iso-BuP(=O)(COMes)$_2$ iso-BuP(COMes)$_2$ obtained in step d) is first taken up in 50 ml of toluene. Water (25 ml) and 2-3 drops of conc. H$_2$SO$_4$ are slowly added at room temperature, such that the pH of the aqueous phase is below a value of four. 6.0 ml of hydrogen peroxide (30% solution in H$_2$O, 0.053 mol, 1.05 eq., M=34.02 g/mol) are added at such a rate that the temperature does not rise above 70° C. The resulting suspension is heated up to 60° C. and kept at this temperature for two hours. The $^{31}$P NMR spectra of the toluene phase shows a new signal at 27 ppm (>83%), identified as iso-BuP(=O)(COMes)$_2$. 20 ml of water are added and the aqueous phase saturated with NaCl. The organic phase is separated, first washed with 20 ml of a 1% aqueous NaHCO$_3$ solution, and then with water (3×15 ml). Drying of the organic phase over MgSO$_4$, filtration and concentration under vacuum gives a yellow oil which is further purified via column chromatography (SiO$_2$, n-hexane/ethyl acetate 4:1). 7.56 g (38%, related to red phosphorous) of iso-BuP(=O)(COMes)$_2$ ($C_{24}H_{31}PO_3$, M=398.47 g/mol) are obtained as a light yellow solid with $R_f$=0.35 (n-hexane/ethyl acetate 4:1).

$^1$H-NMR (300.13 MHz, CDCl$_3$, 25° C.): δ=6.85 (s, 4H, Mes CH), 2.28 (s, 6H, Mes p-CH$_3$), 2.25 (s, 12H, Mes o-CH$_3$), 2.13 (m, 1H, PCH$_2$CH), 2.11 (m, 2H, PCH$_2$), 1.05 (d, $^3J_{HH}$=5.9 Hz, 6H, CHCH$_3$). $^{13}$C{H}-NMR (75.47 MHz,

CDCl$_3$, 25° C.): δ=216.6 (d, $^1J_{CP}$=52.8 Hz, CO), 141.3 (d, $^5J_{CP}$=0.5 Hz, Mes C$^4$), 136.1 (d, $^2J_{CP}$=40.1 Hz, Mes C$^1$), 135.8 (d, $^3J_{CP}$=0.7 Hz, Mes C$^{2,6}$), 129.4 (d, $^4J_{CP}$=0.8 Hz, Mes C$^{3,5}$), 34.4 (d, $^1J_{CP}$=52.5 Hz, PCH$_2$), 24.6 (d, $^3J_{CP}$=8.5 Hz, CHCH$_3$), 23.9 (d, $^2J_{CP}$=4.5 Hz, PCH$_2$CH), 21.4 (s, Mes p-CH$_3$), 19.9 (d, $^4J_{CP}$=0.5 Hz, Mes o-CH$_3$). $^{31}$P{H}-NMR (121.49 MHz, CDCl$_3$, 25° C.): δ=28.2. EA: calculated: [C] 72.34%, [H] 7.84%, [P] 7.77%; found [C] 72.19%, [H] 7.79%, [P] 7.81%. MS (EI): m/z=398 (M$^+$, 0.33%), 251 (M$^+$-MesCO, 1%), 147 (MesCO$^+$, 100%), 119 (Mes$^+$, 7.5%).

Example 2

Preparation of [isobutyl-(2,4,6-trimethyl-benzoyl)-phosphinoyl]-(2,4,6-tri-methyl-phenyl)-methanone using lithium and no proton source (without step b)

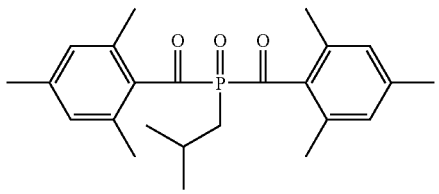

formula I, R$_1$=iso-butyl, R$_2$=mesityl, m=2 a) Preparation of Li$_3$P 0.56 g of lithium powder (81 mmol), 0.84 g of red phosphorous (27 mmol) and 610 mg of naphthalene (4.8 mmol) are suspended in 60 ml of DME. The suspension is heated up to 75° C. and kept at this temperature for 20 h under stirring.

b) None.

c) Preparation of lithium bis(mesitoyl)phosphide×DME, {Li[P(COMes)$_2$]×DME}

The light brown mixture of step a) is cooled down to 30 to 40° C. 10.06 g of 2,4,6-trimethylbenzoyl chloride (54 mmol) are dropwise added. The reaction mixture is left stirring for 3 h at room temperature.

d) Alkylation to iso-BuP(COMes)$_2$ 5.9 g of isobutyl bromide are added portion wise under stirring to the solution obtained in step c) (Reaction temperature 70-80° C.). The reaction mixture is filtered over hyflo (Hyflo Super Cel®; Fluka, Buchs, Switzerland). The filtrate is evaporated to dryness, the residual mass dissolved in toluene and extracted with water and with sodium chloride solution. The organic phase is dried over Na$_2$SO$_4$ and concentrated. 7.43 g of iso-BuP(COMes)$_2$ is obtained as a yellow oil.

e) Oxidation to iso-BuP(=O)(COMes)$_2$

Analogous to step e) in Example 1.

The crude product has been purified via column chromatography (SiO$_2$, n-hexane/ethyl acetate 85:15). 2.36 g (22%, related to red phosphorous) of iso-BuP(=O)(COMes)$_2$ are obtained as a yellow oil which crystallize upon standing.

$^1$H-NMR (CDCl$_3$): δ=6.87 (s; 4H); 2.30 (s; 6H); 2.27 (s; 12H); 2.10-2.17 (m; 3H); 1.07 (d; 6H). $^{31}$P-NMR (CDCl$_3$): δ=29.3

Example 3

Preparation of [methyl-(2,4,6-trimethyl-benzoyl)-phosphanyl]-(2,4,6-tri-methyl-phenyl)-methanone using sodium and tert-butanol

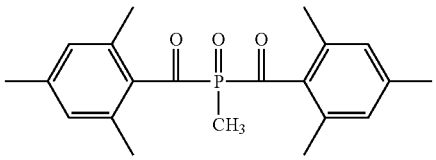

formula I, R$_1$=methyl, R$_2$=mesityl, m=2 a) Preparation of Na$_3$P analogous to Example 1 b) Preparation of NaPH$_2$ analogous to Example 1 c) Preparation of sodium bis(mesitoyl)phosphide×DME, {Na[P(COMes)$_2$]×DME} analogous to Example 1 d) Alkylation to methyl-bis(mesitoyl)phosphane, CH$_3$P(COMes)$_2$

A solution of {Na[P(COMes)$_2$]×DME} in DME prepared according to step c) is concentrated to 80 ml, 7.08 g of methyl iodide (0.05 mol, 1.0 eq., M=141.94 g/mol) are added. The orange suspension is heated up to 60° C. and kept at 60° C. for 2 h under stirring. The $^{31}$P NMR spectrum shows a new signal at 39 ppm (>98%) identified as MeP(COMes)$_2$. The light yellow suspension is filtered through G4/Celite and the filter cake washed once with DME (10 ml). All volatile compounds are removed under high vacuum giving MeP(COMes)$_2$ as a yellow oil.

e) Oxidation to CH$_3$P(=O)(COMes)$_2$, Analogous to Example 1.

The $^{31}$P NMR spectra of the toluene phase shows a new signal at 22.6 ppm (>95%), identified as CH$_3$P(=O)(COMes)$_2$. The crude product has been purified via column chromatography (SiO$_2$, n-hexane/ethyl acetate 4:1). 5.06 g (29%, related to red phosphorous) of CH$_3$P(=O)(COMes)$_2$ (C$_{21}$H$_{25}$O$_3$P, M=356.40 g/mol) are obtained as a light yellow solid with R$_f$=0.2 (n-hexane/ethyl acetate 4:1).

M.p.=126° C. $^1$H-NMR (300.13 MHz, CDCl$_3$, 25° C.): δ=6.86 (s, 4H, Mes CH), 2.29 (s, 6H, Mes p-CH$_3$), 2.27 (s, 12H, Mes o-CH$_3$), 2.11 (d, 3H, $^2J_{PH}$=12.3 Hz, PCH$_3$). $^{13}$C{H}-NMR (75.47 MHz, CDCl$_3$, 25° C.): δ=216.7 (d, $^1J_{CP}$=58.3 Hz, CO), 141.4 (d, $^5J_{CP}$=0.6 Hz, Mes C$^4$), 135.9 (d, $^2J_{CP}$=41.4 Hz, Mes C$^1$), 135.6 (d, $^3J_{CP}$=0.8 Hz, Mes C$^{2,6}$), 129.3 (d, $^4J_{CP}$=0.9 Hz, Mes C$^{3,5}$), 21.4 (s, Mes p-CH$_3$), 19.8 (d, $^4J_{CP}$=0.5 Hz, Mes o-CH$_3$), 12.6 (d, $^1J_{CP}$=56.8 Hz, PCH$_3$). $^{31}$P{H}-NMR (121.49 MHz, CDCl$_3$, 25° C.): δ=23.7. EA: calculated: [C] 70.77%, [H] 7.07%, [P] 8.69%; found [C] 70.69%, [H] 7.14%, [P] 8.70%.

Example 4

Preparation of [methyl-(2,4,6-trimethyl-benzoyl)-phosphanyl]-(2,4,6-tri-methyl-phenyl)-methanone, starting from phosphorous trichloride, using sodium and 3-methyl-3-pentanol

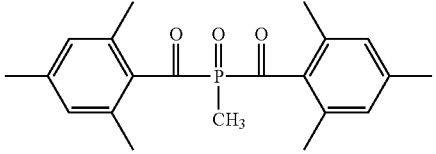

a) Preparation of Na₃P 3.72 g of sodium (162 mmol) and 0.51 g of naphthalene (4 mmol) are suspended in 70 ml of DME. 3.82 g of phosphorous trichloride (27 mmol) in 5 ml of DME is dropwise added within 15 min at room temperature. The suspension is stirred at room temperature overnight, and then for 2 h at 50-60° C., giving a black suspension.

b) Preparation of NaPH₂

The reaction mixture is cooled down to 20° C. and 5.52 g of 3-methyl-3-pentanol (54 mmol) are added within 20 min. Stirring is continued overnight giving a light brown suspension.

c) Preparation of sodium bis(mesitoyl)phosphide×DME, {Na[P(COMes)₂]×DME}

10.06 g of 2,4,6-trimethylbenzoyl chloride (54 mmol) are added within 5-10 min. The reaction mixture is left stirring for 2 h at room temperature giving an orange-white suspension.

d) Alkylation to methyl-bis(mesitoyl)phosphane, CH₃P(COMes)₂

2.74 g of methyl iodide (19 mmol) are added dropwise and left stirring for 2 h at 35-40° C. The resulting white-yellow suspension is filtered over hyflo and concentrated under vacuum. The residue is redissolved in toluene and extracted two times with water and once with saturated aqueous NaCl solution. The organic phase is dried over Na₂SO₄ and concentrated under vacuum. 12.34 g of crude CH₃P(COMes)₂ are obtained as a yellow oil.

e) Oxidation to CH₃P(=O)(COMes)₂

The crude oil is redissolved in 30 ml of toluene and treated with 3.06 g of H₂O₂ (30% in H₂O, 27 mmol) within 5 min at 20° C. Stirring is continued for 30 min. The reaction mixture is diluted and then extracted with water, 2% aqueous NaHCO₃ and saturated NaCl solution, followed by drying over Na₂SO₄ and concentration under vacuum. 9.41 g of yellow oil are stirred in 15 ml hexane during 30 min resulting in the precipitation of a solid which is collected by filtration. Washing with cold hexane and drying under high vacuum provides 3.85 g (40%, related to red phosphorous) of a white-yellow solid. An additional 0.27 g solid (3%) has been isolated from the mother liquor.

Example 5

Preparation of [methyl-(2,4,6-trimethyl-benzoyl)-phosphanyl]-(2,4,6-tri-methyl-phenyl)-methanone using lithium and 3-methyl-3-pentanol a) Preparation of Li₃P analogous Example 2, with 1.04 g of naphthalene (8.1 mmol)

b) Preparation of LiPH₂

The mixture of step a) is cooled down to 0 to 10° C. A solution of 5.58 g of 3-methyl-3-pentanol (54 mmol) in 5 ml of DME are added within 45 min under stirring. The reaction mixture is left stirring for another 120 min without cooling.

c) Preparation of lithium bis(mesitoyl)phosphide×DME, {Li[P(COMes)₂]×DME}

10.06 g of 2,4,6-trimethylbenzoyl chloride (54 mmol) are dropwise added to the reaction mixture of step b) at 10-20° C. within 25 min. The reaction mixture is left stirring for 40 min at room temperature.

d) Alkylation to CH₃P(COMes)₂

The resulting thin brown-red suspension from step c) is dropwise treated with 5.75 g of methyl iodide (40.5 mmol) during 10 min under stirring. The reaction mixture is left stirring for another 100 min at 40° C., then filtered and concentrated under vacuum. The residue is dissolved in toluene (150 ml) and extracted with water (4×). The toluene phase has been further treated as described in step e).

e) Oxidation to CH₃P(=O)(COMes)₂

Analogous to step e) in Example 1.

The crude product (10.3 g) has been purified via column chromatography (SiO₂, heptane/ethyl acetate 1:1). 1.82 g (19%, related to red phosphorous) of CH₃P(=O)(COMes)₂ are obtained as a light yellow solid.

¹H-NMR (CDCl₃): δ=6.88 (s, 4H); 2.30 (s, 6H); 2.29 (s, 12H); 1.81-1.85 (d, 3H). ³¹P-NMR (CDCl₃): δ=24.8.

Example 6

Preparation of [methyl-(2,4,6-trimethyl-benzoyl)-phosphanyl]-(2,4,6-tri-methyl-phenyl)-methanone using lithium and no proton source (without step b)

a) Preparation of Li₃P analogous to Example 2 with 0.51 g of naphthalene (4 mmol)

b) None.

c) Preparation of lithium bis(mesitoyl)phosphide×DME, {Li[P(COMes)₂]×DME}

10.06 g of 2,4,6-trimethylbenzoyl chloride (54 mmol) are dropwise added to the light brown reaction mixture of step a) at 30-40° C. within 40 min. The reaction mixture is left stirring for 2.5 h at room temperature.

d) Alkylation to CH₃P(COMes)₂

4.22 g of methyl iodide (29.7 mmol) are added within 15 min under stirring at 25-35° C. to the solution obtained in step c). The reaction mixture is left stirring for 20 h at 40° C., cooled down to room temperature and then filtered over hyflo (Hyflo Super Cel®; Fluka, Buchs, Switzerland). The resulting filtrate is concentrated under vacuum, the residue dissolved in toluene and extracted three times with water and with saturated sodium chloride solution. The organic phase is dried over Na₂SO₄ and concentrated under vacuum. 6.76 g of crude CH₃P(COMes)₂ are obtained as a yellow oil.

e) Oxidation to CH$_3$P(=O)(COMes)$_2$

Analogous to step e) in Example 2.

The crude product (5.32 g) has been purified via column chromatography (SiO$_2$, heptane/ethyl acetate 1:1). 1.27 g (13%, related to red phosphorous) of CH$_3$P(=O)(COMes)$_2$ are obtained as a white solid.

$^1$H-NMR (CDCl$_3$): δ=6.88 (s, 4H); 2.30 (s, 6H); 2.29 (s, 12H); 1.81-1.85 (d, 3H). $^{31}$P-NMR (CDCl$_3$): δ=24.8.

Example 7

Preparation of [benzyl-(2,4,6-trimethyl-benzoyl)-phosphanyl]-(2,4,6-tri-methyl-phenyl)-methanone using lithium and 3-methyl-3-pentanol

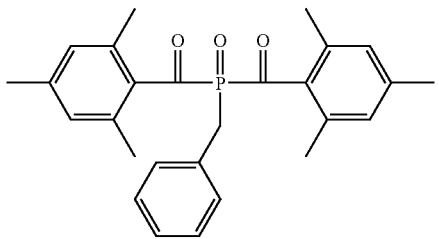

formula I, R$_1$=benzyl, R$_2$=mesityl, m=2 a) Preparation of Li$_3$P 104 mg of lithium granulate (15 mmol), 155 mg of purified red phosphorous (5 mmol) and 64 mg of naphthalene (0.5 mmol) are suspended in 20 ml of DME. The suspension is heated to 70-80° C. and kept at this temperature for 16 h under stirring.

b) Preparation of LiPH$_2$

Analogous to Example 4, with 1.02 g of 3-methyl-3-pentanol (10 mmol).

c) Preparation of lithium bis(mesitoyl)phosphide×DME, {Li[P(COMes)$_2$]×DME}

Analogous to Example 4, with 1.83 g of 2,4,6-trimethyl-benzoyl chloride (10 mmol).

d) Alkylation to benzyl-P(COMes)$_2$ 1.31 g of benzyl bromide (7.5 mmol) are added to the thin light brown suspension obtained in step c) within 15 min under stirring. The reaction mixture is left stirring for another 2.5 h at 50-60° C. DME is removed under vacuum and the residue taken up in toluene (40 ml).

e) Oxidation to benzyl-P(=O)(COMes)$_2$

Analogous to step e) in Example 1.

The crude product (2.3 g) has been purified via column chromatography (SiO$_2$, heptane/ethyl acetate 60:40). 207 mg of benzyl-P(=O)(COMes)$_2$ are obtained as a yellow viscous oil.

$^1$H-NMR (CDCl$_3$): δ=7.25-7.32 (m, 5H); 6.82 (s, 4H); 3.60-3.64 (d, 2H); 2.28 (s, 6H); 2.08 (s, 12H). $^{31}$P-NMR (CDCl$_3$): δ=24.1.

Example 8

Preparation of [(4,4,4-trifluoro-2-methyl-butyl)-(2,4,6-trimethyl-benzoyl)-phosphinoyl]-(2,4,6-trimethyl-phenyl)-methanone using sodium and tert-butanol

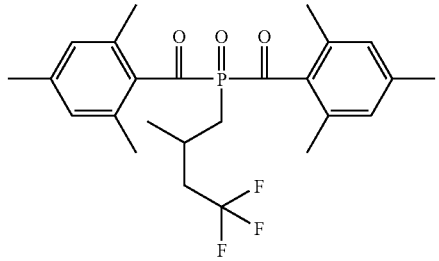

formula I, R$_1$=4,4,4-trifluoro-2-methyl-butyl, R$_2$=mesityl, m=2 a) Preparation of Na$_3$P

Analogous to Example 1.

b) Preparation of NaPH$_2$

Analogous to Example 1.

c) Preparation of sodium bis(mesitoyl)phosphide×DME, {Na[P(COMes)$_2$]×DME}

Analogous to Example 1.

d) preparation of [CF$_3$—CH$_2$—CH(CH$_3$)—CH$_2$]P(COMes)$_2$ 2.2 g of {Na[P(COMes)$_2$]×DME} (5.0 mmol, M=438.47 g/mol) obtained according to step 1c) are dissolved in 40 ml of toluene and 30 ml of DME. 1.7 g of 1-bromo-2-methyl-4,4,4-trifluorobutane (1.66 eq., 8.3 mmol, M=205.02 g/mol) are added. The reaction mixture is stirred at 80° C. for 72 h. The $^{31}$P-NMR spectra shows no more signal of the starting material and a new signal at 45.7 ppm. The light yellow suspension is filtered through G4/Celite. The filtrate solution is concentrated to 50 ml.

e) Oxidation to [CF$_3$—CH$_2$—CH(Me)—CH$_2$]P(=O)(COMes)$_2$

Analogous to Example 1

The $^{31}$P NMR spectra of the toluene phase shows a new signal at 26.4 ppm. The crude product has been purified via column chromatography (SiO$_2$, n-hexane/ethyl acetate 7:2). 1.05 g (45%, related to red phosphorous) of [CF$_3$—CH$_2$—CH(CH$_3$)—CH$_2$]P(=O)(COMes)$_2$ (C$_{25}$H$_{30}$F$_3$O$_3$P, M=466.47 g/mol) are obtained as a yellow oil with R$_f$=0.4 (n-hexane/ethyl acetate 7:2). The yellow oil solidifies after several days storage in the fridge.

M.p.=78° C. $^1$H-NMR* (250.13 MHz, CDCl$_3$, 25° C.): δ=6.84 (s, 4H, Mes CH), 2.40 (m, 2H, CH$_2$CF$_3$), 2.26 (s, 6H, Mes p-CH$_3$), 2.23 (s, 6H, Mes o-CH$_3$), 2.20 (s, 6H, Mes o-CH$_3$), 2.18 (m, 2H, PCH$_2$), 2.04 (m, 1H, PCH$_2$CH), 1.16 (d, $^3$J$_{HH}$=6.3 Hz, 3H, CHCH$_3$). $^{13}$C{H}-NMR* (62.90 MHz, CDCl$_3$, 25° C.): δ=215.8 (d, $^1$J$_{CP}$=52.4 Hz, CO), 215.4 (d, $^1$J$_{CP}$=52.7 Hz, CO), 141.5 (d, $^5$J$_{CP}$=0.6 Hz, Mes C$^4$), 141.5 (d, $^5$J$_{CP}$=0.6 Hz, Mes C$^4$), 135.8 (d, $^3$J$_{CP}$=0.7 Hz, Mes C$^{2,6}$), 135.7 (d, $^3$J$_{CP}$=0.7 Hz, Mes C$^{2,6}$), 135.7 (d, $^2$J$_{CP}$=40.6 Hz, Mes C$^1$), 135.6 (d, $^2$J$_{CP}$=40.7 Hz, Mes C$^1$), 129.3 (s, Mes C$^{3,5}$), 129.3 (s, Mes C$^{3,5}$), 126.5 (q, $^1$J$_{CF}$=277.3 Hz, CF$_3$), 40.8 (q, $^2$J$_{CF}$=27.5 Hz, CH$_2$CF$_3$), 40.7 (q, $^2$J$_{CF}$=27.5 Hz, CH$_2$CF$_3$), 32.0 (d, $^1$J$_{CP}$=52.9 Hz, PCH$_2$), 23.7 (br., PCH$_2$CH), 21.9 (d, $^3$J$_{CP}$=7.3 Hz, CHCH$_3$), 21.2 (s, Mes p-CH$_3$), 21.2 (s, Mes p-CH$_3$), 19.8 (d, $^4$J$_{CP}$=0.4 Hz, Mes o-CH$_3$), 19.7 (d, $^4$J$_{CP}$=0.4 Hz, Mes o-CH$_3$). $^{19}$F-NMR (CDCl$_3$, 25° C.): δ=−63.1 (m, CF$_3$). $^{31}$P{H}-NMR (101.25 MHz, CDCl$_3$, 25° C.): δ=26.4. MS (EI): m/z=466 (M$^+$, 3%), 319 (M$^+$-MesCO, 26%), 147.5 (MesCO$^+$, 100%), 119.2 (Mes$^+$, 63%).

Example 9

Preparation of [{3-[bis-(2,4,6-trimethyl-benzoyl)-phosphinoyl]-propyl}-(2,4,6-trimethyl-benzoyl)-phosphinoyl]-(2,4,6-trimethyl-phenyl)-methanone using lithium and no proton source

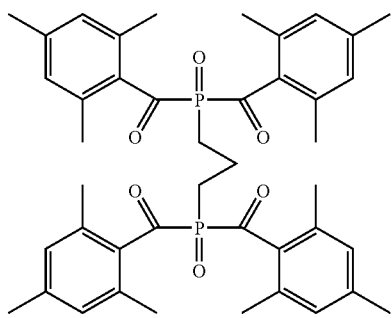

Formula I, n=2, $R_1$=propylene, $R_2$=mesityl, m=2 a) Preparation of $Li_3P$

Analogous to Example 2, with 0.51 g of naphthalene (4 mmol).

b) None.

c) Preparation of lithium bis(mesitoyl)phosphide×DME, {Li[P(COMes)$_2$]×DME}

Analogous to Example 2.

10.06 g of 2,4,6-trimethylbenzoyl chloride (54 mmol) are dropwise added to the light brown reaction mixture of step a) at 30-40° C. within 30 min. The reaction mixture is left stirring for 1.5 h at 40-50° C.

d) Alkylation to

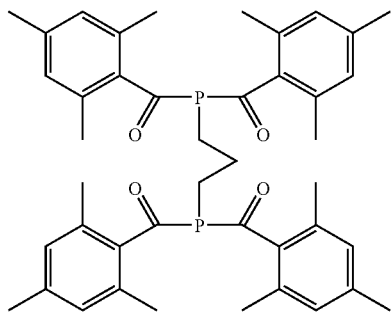

0.91 g of 1,3-diiodopropane (3.0 mmol) are added within 5 min under stirring at 40-50° C. to the solution obtained in step c). The reaction mixture is stirred for 40 min at the same temperature, and then for 6 h at 60-70° C. An additional 0.91 g of diiodopropane (3.0 mmol) are added within 5 min and the resulting reaction mixture left stirring for another 22 h at 60-70° C. After cooling down to 30-40° C., 0.87 g of methanol (27 mmol) are added and stirring continued for one hour at the same temperature. The reaction mixture is cooled down to room temperature and filtered over hyflo (Hyflo Super Cel®; Fluka, Buchs, Switzerland). The resulting filtrate is concentrated under vacuum, the residue dissolved in toluene and extracted three times with water and with saturated sodium chloride solution. The organic phase is dried over $Na_2SO_4$ and concentrated under vacuum. 7.7 g of an orange oil are obtained.

e) Oxidation analogous to step e) in Example 1.

The crude product (5.32 g) has been purified via column chromatography ($SiO_2$, heptane/ethyl acetate 1:1) giving 1.52 g of a white solid. The solid has been further stirred in hexane, separated and then dried under high vacuum giving 1.24 g (13%, related to red phosphorous) of the title compound as a yellow solid.

$^1$H-NMR (CDCl$_3$): δ=6.85 (s; 8H); 2.23-2.37 (m; 4H); 2.28 (s; 12H); 2.23 (s; 24H); 1.95-2.10 (m; 2H). $^{31}$P-NMR (CDCl$_3$): δ=26.7.

Example 10

Preparation of [Phenyl-(2,4,6-trimethyl-benzoyl)-phosphinoyl]-(2,4,6-tri-methyl-phenyl)-methanone (=Irgacure 819)

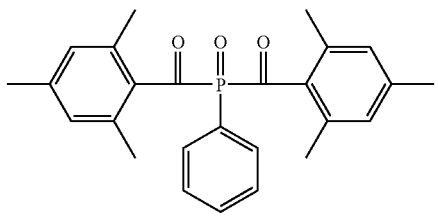

formula I, $R_1$=phenyl, $R_2$=mesityl, m=2 a) preparation of $Na_3P$ analogous to Example 1
b) preparation of $NaPH_2$ analogous to Example 1
c) preparation of sodium bis(mesitoyl)phosphide×DME, {Na[P(COMes)$_2$]×DME} analogous to Example 1
d) preparation of phenyl-bis(mesitoyl)phosphane, phenyl-P(COMes)$_2$ One equivalent of phenyl iodide is added together with 1 mol % of Pd(PPh$_3$)$_4$. The reaction mixture is left stirring for 24 h at 60° C., showing 25% conversion according to the $^{31}$P-NMR spectra. Afterwards, the reaction mixture is left stirring for an additional 48 h giving a conversion of 33%.

e) Oxidation analogous to step e) in Example 1 provides [phenyl-(2,4,6-trimethyl-benzoyl)-phosphinoyl]-(2,4,6-tri-methyl-phenyl)-methanone (=Irgacure 819) as yellowish solid.

Example 11

Preparation of Alcoholate Cluster of Phosphide from Red Phosphorus Using Sodium and tert-butanol

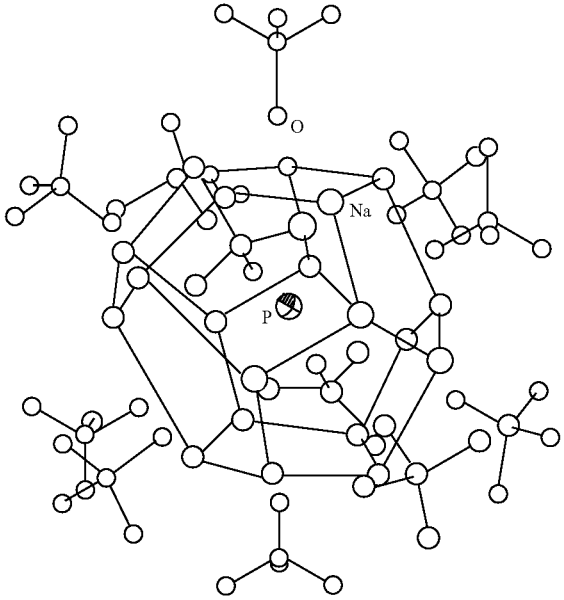

0.194 g of purified red phosphorus (6.26 mmol, 1 eq., M=30.97 g/mol) and 0.5 g of sodium sand (21.75 mmol, 3.47 eq., M=22.99 g/mol) are grinded under argon atmosphere in an agate mortar providing a dark grey, viscous mass. The mixture is then heated under argon up to 300° C. during 2 min in a Schlenk-tube giving a grey-black powder. The powder is then suspended in 10 ml of dimethoxyethane followed by dropwise addition of 1.147 g tert-butanol (15.47 mmol). The reaction is accompanied by vigorous gas evolution. The grey suspension is then stirred for 4 h at room temperature and the resulting grey-brown suspension filtered over Celite. The clear beige solution is concentrated under vacuum and the resulting light beige powder suspended in 10 ml of toluene. The suspension is heated up until a clear beige solution is formed. Octahedral crystals separate which are collected by filtration and then washed with 2 ml of toluene. 0.95 g of product (13% related to NaPH$_2$) are obtained as a colorless solid.

The product is characterized by x-ray structure analysis and corresponds to an alcoholate cluster with the formula [Na$_{13}$(O$^t$Bu)$_{12}$@PH$_2$]: (C$_{48}$H$_{110}$Na$_{13}$O$_{12}$P, M=1209.22 g/mol)].

$^1$H-NMR (300.13 MHz, C$_6$D$_6$, 25° C.): δ=1.49 (s, 110H, $^t$Bu), −2.18 (d, 2H, $^1J_{P,H}$=142.5 Hz). $^{31}$P-NMR (121.47 MHz, C$_6$D$_6$, 25° C.): δ=−292.3 (t, $^1J_{P,H}$=142.5 Hz)

Example 12

Preparation of Alcoholate Cluster of Phosphide by the Reaction of Sodium tert-butoxide with Sodium Phosphide NaPH$_2$ has been first prepared according to Brauer, "Handbuch der Präparativen Anorganischen Chemie", Bd I, p. 510.

Afterwards, 1.03 g sodium tert-butoxide (10.7 mmol, 12 eq., M=96.10 g/mol) and 50 mg NaPH$_2$ (0.89 mmol, 1 eq., M=55.98 g/mol) are suspended in 15 mol of toluene. The beige suspension is kept for 24 hours at room temperature. Colorless, octahedral crystals separate from the reaction mixture which are collected by filtration and further washed with 2 ml of toluene. 0.85 g of product (78% related to NaPH$_2$) are obtained as a colorless solid.

The same analytical data are obtained like the product from example 11, corresponding to the formula [Na$_{13}$(O$^t$Bu)$_{12}$@PH$_2$]: (C$_{48}$H$_{110}$Na$_{13}$O$_{12}$P, M=1209.22 g/mol)].

Example 13

Preparation of sodium bis(mesitoyl)phosphide {Na[P(COMes)$_2$]} or sodium bis(mesitoyl)phosphide×DME {Na[P(COMes)$_2$]×DME} from [Na$_{13}$(O$^t$Bu)$_{12}$@PH$_2$]

1 g of [Na$_{13}$(O$^t$Bu)$_{12}$@PH$_2$] from example 12 (0.83 mmol, 1 eq., M=1209.22 g/mol) is dissolved in toluene (the same experiment has been also run in DME). The resulting mixture is cooled over an ice-bath. 0.3 g of 2,4,6-trimethylbenzoyl chloride (TMBCl) in 5 ml of toluene are added dropwise. Stirring is continued for 30 min at room temperature. All volatile compounds have been removed at 0.1 Torr and the yellow-orange residue taken up in toluene. Subsequent filtration and crystallization from toluene/n-hexane leads to {Na[P(COMes)$_2$]}. Furthermore, {Na[P(COMes)$_2$]×DME} has been isolated when DME was used instead of toluene for the same procedure.

This complex can be further alkylated as e.g. in Example 1d).

Example 14

Preparation of 2,4,6-trimethylbenzoyl-pivaloyl-methylphosphine

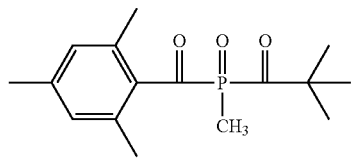

Formula I, R$_2$=mesityl, R$_2$=t.butyl 0.5 g of NaPH$_2$ (8.9 mmol, 1 eq., M=55.98 g/mol), prepared according to example 11, are suspended in 30 ml of toluene. 1.575 g of methyl 2,4,6-trimethylbenzoate (8.9 mmol, 1 eq., M=178.23 g/mol) in 10 ml of THF are dropwise added and stirring is continued for 30 min at room temperature. The resulting yellow suspension is filtered and then concentrated under high vacuum giving a yellow oil.

The oil is taken up in 20 ml of THF and dropwise treated at room temperature with 0.807 g of pivaloyl chloride (2,2-dimethylpropionyl chloride) (6.7 mmol, 0.75 eq., M=120.58 g/mol) in 10 ml of THF. The yellow suspension is stirred for 30 min at room temperature. 0.855 g of sodium tert-butoxide (8.9 mmol, 1 eq., M=96.10 g/mol) are added in several portions providing a yellow-orange suspension. After stirring for 30 min at room temperature 0.55 ml of methyl iodide (8.9 mmol, 1 eq., M=141.94 g/mol) are dropwise added giving an almost colorless suspension. Stirring is continued for an additional hour at room temperature. The reaction mixture is concentrated under vacuum and then taken up in 20 ml of toluene, filtered over Celite and additional rinsing with 10 ml of toluene. $^{31}$P-NMR analysis shows one resonance at 23.7 ppm for 2,2-dimethyl-1-[methyl-(2,4,6-trimethyl-benzoyl)-phosphanyl]-propan-1-one.

To the resulting solution is added 10 ml of water and 2.01 g of 30% H$_2$O$_2$ solution (17.8 mmol, 2 eq., M=34.01 g/mol). The reaction mixture is stirred for 4 h at 30° C. The organic phase is washed three times with 10 ml of water and the aqueous phases washed with 20 ml of toluene. The combined organic phases are dried over MgSO$_4$ and then concentrated under vacuum. The resulting yellow oil is purified by flash chromatography (hexane/ethyl acetate 1:1, R$_f$=0.45). Yield: 0.69 g yellow oil (26%, C$_{16}$H$_{23}$O$_3$P, M=294.33 g/mol)

$^1$H-NMR (300.13 MHz, CDCl$_3$, 25° C.): δ=6.88 (s, 2H, Mes CH), 2.30 (s, 3H, Mes p-CH$_3$), 2.29 (s, 6H, Mes o-CH$_3$), 1.76 (d, $^2J_{P,H}$=12.6 Hz, PCH$_3$), 1.28 (s, 9H, $^t$Bu). $^{13}$C{H}-NMR (75.47 MHz, CDCl$_3$, 25° C.): δ=220.9 (d, $^1J_{CP}$=43.1 Hz, $^t$BuCO), 215.2 (d, $^1J_{CP}$=57.7 Hz, MesCO), 140.7 (d, $^5J_{CP}$=0.8 Hz, Mes C$^4$), 136.1 (d, $^2J_{CP}$=42.3 Hz, Mes C$^1$), 134.6 (d, $^3J_{CP}$=0.6 Hz, Mes C$^{2,6}$), 129.0 (d, $^4J_{CP}$=0.7 Hz, Mes C$^{3,5}$), 48.6 (d, $^2J_{CP}$=37.6 Hz, C(CH$_3$)$_3$), 24.3 (s, C(CH$_3$)$_3$), 21.2 (s, Mes p-CH$_3$), 19.8 (s, Mes o-CH$_3$), 12.9 (d, $^1J_{CP}$=57.4 Hz, PCH$_3$). $^{31}$P-NMR (121.5 MHz, CDCl$_3$, 25° C.): δ=28.2 (q, $^2J_{P,H}$=12.6 Hz).

Example 15

Preparation of acetic acid 3-[bis-(2,6-dimethoxy-benzoyl)-phosphinoyl]-propyl ester, starting from phosphorus trichloride

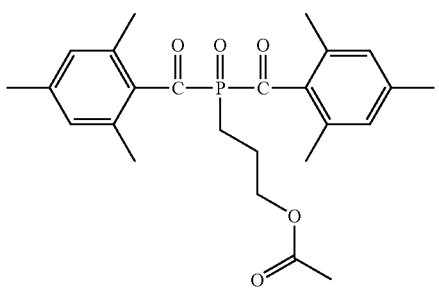

Formula I, $R_1$=propyl substituted by —OCO-methyl; $R_2$=mesityl, m=2 a) Preparation of $Na_3P$ 3.72 g of sodium (162 mmol) and 0.51 g of naphthalene (4 mmol) are suspended in 70 ml of DME. 3.82 g of $PCl_3$ (27 mmol) is dropwise added within 15 min at room temperature. The suspension is stirred at room temperature overnight, giving a black suspension.

b) Preparation of $NaPH_2$

To the reaction mixture 5.52 g of 3-methyl-3-pentanol (54 mmol) are added dropwise within 3 hours. Stirring is continued for an additional 5.5 hours at room temperature, giving a light brown suspension.

c) Preparation of sodium bis(mesitoyl)phosphide×DME, {Na[P(COMes)$_2$]×DME}

10.06 g of 2,4,6-trimethylbenzoyl chloride (54 mmol) are added dropwise within 30 min. The reaction mixture is left stirring over night at room temperature giving an orange-yellow suspension.

d) Alkylation to acetic acid 3-[bis-(2,4,6-trimethyl-benzoyl)-phosphanyl]-propyl ester 29.7 mmol of 3-bromopropylacetate (synthesised analogue to 6-bromohexylacetate according to literature: Z. Naturforsch. 55 b; 2000; p 583) are added dropwise within 10 min. and left stirring for 2.5 h at 50-60° C. The resulting yellow suspension is taken to dryness and resolved in 100 ml toluene (yellow suspension).

$^{31}$P-NMR ($d_6$-benzene): 53.2 ppm (bisacyl-alkylphosphine)

e) Oxidation 60 ml water are added to the crude reaction mixture. The pH is adjusted with 2 molar HCl to 5-7 and treated with 4.46 g of hydrogen peroxide (30% in $H_2O$, 40.5 mmol) within 5 min at room temperature. After heating to 50-60° C. stirring is continued for 2 h. The reaction mixture is separated and the organic layer is extracted with 2% aqueous $NaHCO_3$ and saturated NaCl solution, followed by drying over $Na_2SO_4$ and concentration under vacuum. The crude 13.86 g yellow oil is purified by preparative chromatography (heptane/ethylacetate 1:1; silicagel), to give 4.34 g 3-[bis-(2,4,6-trimethyl-benzoyl)-phosphinoyl]-propyl acetate as a yellow oil (yield 36%).

$^{31}$P-NMR ($CDCl_3$): 27.5 ppm

Examples 16-31 (Table 1) are prepared using the same reaction sequence, expect that in step d the alkylating agent listed in Table 1 is used instead of 3-bromopropylacetate.

TABLE 1

| Ex. | alkylating agent | $R_1$ | $^{31}$P-NMR ($C_6D_6$) ppm | $^{31}$P-NMR ($CDCl_3$) ppm | yield | mp [° C.] |
|---|---|---|---|---|---|---|
| 16 | 6-bromohexyl acetate | | 53.5 | 29.0 | 43% | 62-64 |
| 17 | methyl bromo-acetate | | 47.7 | 18.1 | 41%[c] | 105-107 |
| 18 | ethyl chloro-acetate | | 47.1 | 18.4 | 51%[c] | 92-94 |
| 19 | ethyl 2-bromo-propionate | | 74.18 | 25.4 | 25%[c] | 89-90 |

TABLE 1-continued

[Structure: bis(mesitoyl)phosphine with R₁ substituent on P]

| Ex. | alkylating agent | R₁ | ³¹P-NMR (C₆D₆) ppm | ³¹P-NMR (CDCl₃) ppm | yield | mp [° C.] |
|---|---|---|---|---|---|---|
| 20 | n-octyl 2-bromo-acetate | –CH₂–C(=O)–O–(CH₂)₇CH₃ | 47.6 | 19.4 | 12%[e] | oil |
| 21 | t.butyl bromo-acetate | –CH₂–C(=O)–O–C(CH₃)₃ | 46.3 | 19.1 | 49%[b] | 81-83 |
| 22 | vinyl chloro-acetate | –CH₂–C(=O)–O–CH=CH₂ | 47.9 | 18.4 | 44%[c] | 88-91 |
| 23 | dimethyl-sulfate | —CH₃ | 40.8 | 23.7 | 44%[c] | 126 |
| 24 | 4-bromo-1-butene | –CH₂CH₂CH=CH₂ | 52.5 | 27.9 | 34%[e] | oil |
| 25 | 3-bromo-propionitrile | –CH₂CH₂–C≡N | 51.6 | 21.7 | 27%[c] | 124-127 |
| 26 | benzyl 2-bromoethyl ether | –CH₂CH₂–O–CH₂–C₆H₅ | 46.0 | 25.5 | 38%[d] | oil |
| 27 | 2-bromo-eth-oxy-tetra-hydropyrane | –CH₂CH₂–O–(tetrahydropyran-2-yl) | 46.1 | 25.1 | 18%[a] | oil |
| 28 | 2-bromoethyl methacrylate | –CH₂CH₂–O–C(=O)–C(CH₃)=CH₂ | 47.1 | 24.4 | 13%[d] | oil |
| 29 | epibrom-hydrine | –CH₂–(epoxide) | 47.4 | 22.1 | 21%[f] | oil |
| 30 | N-bromo-methyl-phthalimide | –CH₂–N(phthalimide) | 45.3 | 13.2 | 71%[c] | 160-164 |
| 31 | α-bromo-acetophenone | –CH₂–C(=O)–C₆H₅ | 46.7 | 21.0 | 28%[c] | 95-98 |

[a] after prep-chromatographie (heptane/ethylacetat 3:7; silicagel),
[b] after crystallisation from petrolether

TABLE 1-continued

| | | $^{31}$P-NMR $(C_6D_6)$ | $^{31}$P-NMR $(CDCl_3)$ | | |
|---|---|---|---|---|---|
| Ex. | alkylating agent  $R_1$ | ppm | ppm | yield | mp [° C.] |

$^{c)}$after prep-chromatographie (heptane/ethylacetat 3:7; silicagel),
$^{d)}$after crystallisation from petrolether
$^{e)}$after crystallisation from hexane
$^{f)}$after prep-chromatographie (heptane/ethylacetat 6:4; silicagel),
$^{g)}$after prep-chromatographie (heptane/ethylacetat 7:3; silicagel),
$^{h)}$after prep-chromatographie (heptane:ethylacetat 1:1; silicagel),
$^{i)}$after prep-chromatographie (heptane:ethylacetat 4:6; silicagel),

Example 32

Preparation of [bis-(2,4,6-trimethyl-benzoyl)-phosphanyl]-acetic acid ethyl ester starting from red phosphorus in ammonia

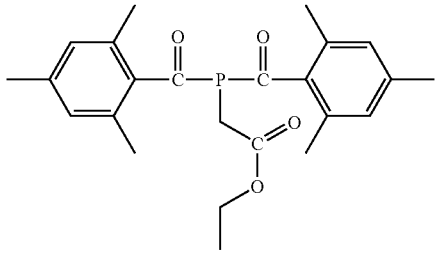

a. Preparation of NaPH$_2$ 1.725 g (0.075 mol, 3 equivalents) Sodium sand are dissolved in 50 ml liquid ammonium at −70° C. under argon. To this solution, a suspension of 0.775 g (0.025 mol, 1 equivalent) purified red phosphorus (grounded to ≦230 Mesh) in tetrahydrofuran is slowly added over 1 hour. The bluish-red suspension is stirred for 3 hours, keeping the temperature between −55 and −65° C., while a reddish-beige solid is deposited from the reaction mixture. This solid is dissolved upon the addition of 4.8 ml tert-butanol (0.05 mol, 2 equivalents) in 7 ml tetrahydrofuran at −60° C. over 1.5 hours. The blue solution is stirred for 2.5 hours at −60° C., during which time the color changes to green and finally ochre. The solution is slowly warmed to room temperature over a time of 4 hours. The $^{31}$P-NMR spectrum of the solution shows a resonance line at −297 ppm (t, $^1$J(P, H)=155 Hz, NaPH$_2$).

b. Preparation of sodium bis(mesitoyl)phosphidexDME, {Na[P(COMes)$_2$]×DME}

The volatile components of the reaction mixture obtained according to example 32a are evaporated in vacuum and the residual ochre solid is dissolved in 60 ml dimethoxyethane (DME). 9.15 g (0.05 mol, 2 equivalents) of 2,4,6-trimethyl-benzoyl chloride are slowly added at room temperature over one hour, resulting in a color change of the suspension to yellow and a slight increase of the temperature. The reaction mixture is stirred for another hour at room temperature. A single resonance at 81.6 ppm in the $^{31}$P-NMR spectrum shows the formation of sodium bis (mesitoyl)phosphidex DME, {Na[P(COMes)$_2$]×DME}, in high yield.

c. Alkylation to [Bis-(2,4,6-trimethyl-benzoyl)-phosphanyl]-acetic acid ethyl ester 4.175 g (0.025 mol. 1 equivalent) bromacetic acid ethyl ester are added over 15 minutes to the solution obtained in step b. After stirring, the solvent and all volatile compounds are removed under vacuum. [Bis-(2,4,6-trimethyl-benzoyl)-phosphanyl]-acetic acid ethyl ester is obtained as a beige solid in 60% yield (Referent to the red phosphorus starting material). The $^{31}$P-NMR spectrum shows the formation this product in high purity by a single resonance line at 46.5 ppm.

Example 33

Preparation of acetic acid 3-[bis-(2,6-dimethoxy-benzoyl)-phosphinoyl]-propyl ester, starting from phosphorus trichloride

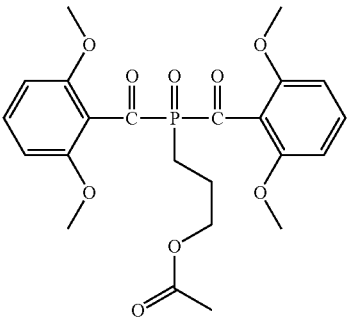

a) Preparation of Na$_3$P 3.72 g of sodium (162 mmol) and 0.51 g of naphthalene (4 mmol) are suspended in 70 ml of DME. 3.82 g of phosphorus trichloride (27 mmol) are dropwise added within 15 min at room temperature. The suspension is stirred at room temperature overnight, giving a black suspension.

b) Preparation of NaPH$_2$

To the reaction mixture 5.52 g of 3-methyl-3-pentanol (54 mmol) dissolved in 10 ml DME are added dropwise within 3 hours. Stirring is continued for an additional 5.5 hours at room temperature, giving a light brown suspension.

c) Preparation of sodium bis(2,6-dimethoxybenzoyl)phosphide×DME, 10.83 g of 2,6 Dimethoxybenzoylchloride (54 mmol) dissolved in 20 ml DME are added dropwise within 50 min. The reaction mixture is left stirring over night at room temperature giving a brown-yellow suspension.

d) Alkylation to acetic acid 3-[bis-(2,6-dimethoxy-benzoyl)-phosphanyl]-propyl ester 29.7 mmol of 3-bromopropylacetate (synthesised analogously to 6-bromohexylacetate reported in Z. Naturforsch. 55 b; 2000; p 583) are added drop wise within 10 min. and left stirring for 3 h at 50-60° C. The resulting yellow suspension is taken to dryness and resolved in 80 ml toluene (yellow suspension).

$^{31}$P-NMR (C$_6$D$_6$): 55.4 ppm (Bisacyl-alkylphosphine)

e) Oxidation 50 ml water are added to the crude reaction mixture. 4.46 g of hydrogen peroxide (30% in H$_2$O, 40.5 mmol) are added within 5 min at room temperature. After heating to 50-60° C. stirring is continued for 1 h. The reaction mixture is separated and the organic layer is extracted with 2% aqueous NaHCO$_3$ and saturated NaCl solution, followed by drying over Na$_2$SO$_4$ and concentration under vacuum. The crude 13.77 g yellow oil is purified by crystallisation from hexane, resulting in 6.76 g acetic acid 3-[bis-(2,6-dimethoxy-benzoyl)-phosphinoyl]-propyl ester as white yellow crystals (yield 52%).

$^{31}$P-NMR(CDCl$_3$): 27.0 ppm

Examples 34-36 (Table 2) are prepared using the same reaction sequence as for sample 3, expect that in step d the alkylating agent listed in Table 1 is used instead of 3-bromopropylacetate.

Example 37

Preparation of acetic acid 3-[bis-(2,6-dichloro-benzoyl)-phosphinoyl]-propyl ester, starting from phosphorus trichloride

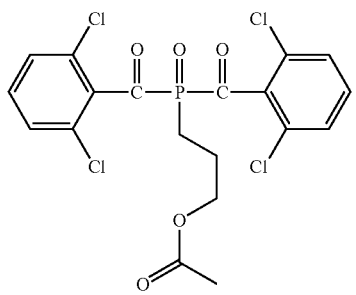

a) Preparation of Na$_3$P 3.72 g of sodium (162 mmol) and 0.51 g of naphthalene (4 mmol) are suspended in 65 ml of DME. 3.82 g of phosphorus trichloride (27 mmol) dissolved in 5 ml DME is dropwise added within 10 min at room temperature. The suspension is stirred at room temperature overnight, giving a black suspension.

b) Preparation of NaPH$_2$

To the reaction mixture 5.52 g of 3-methyl-3-pentanol (54 mmol) dissolved in 10 ml DME are added drop wise within 1.5 hours. Stirring is continued for an additional 5 hours at room temperature, giving a light brown suspension.

TABLE 2

| Ex. | alkylating agent | R$_1$ | $^{31}$P-NMR (C$_6$D$_6$) ppm | $^{31}$P-NMR (CDCl$_3$) ppm | yield | mp [° C.] |
|---|---|---|---|---|---|---|
| 34 | ethyl chloroacetate | ![structure] | 48.1 | 17.9 | 50%[a] | 162-165 |
| 35 | t. butyl bromoacetate | ![structure] | 48.3 | 20.0 | 50%[a] | 76-79 |
| 36 | tert-butyl 3-bromopropionate | ![structure] | 53.6 | 26.2 | 47%[a] | 110 |

[a] after crystallisation from hexane c) Preparation of sodium bis(2,6-dichlorobenzoyl)phosphide×DME, 11.31 g of 2,6 Dichlorobenzoylchloride (54 mmol) dissolved in 10 ml DME are added drop wise within 60 min. The reaction mixture is left stirring over night at room temperature giving a yellow-brown suspension.

d) Alkylation to acetic acid 3-[bis-(2,6-dichloro-benzoyl)-phosphanyl]-propyl ester 29.7 mmol of 3-bromopropylacetate (synthesised analogously to 6-bromohexylacetate reported in Z. Naturforsch. 55 b; 2000; p 583) are added drop wise within 10 min. and left stirring for 8 h at 50-60° C. The resulting yellow suspension is taken to dryness and resolved in 80 ml toluene (yellow suspension).

$^{31}$P-NMR ($C_6D_6$): 48.8 ppm (Bisacyl-alkylphosphine)

e) Oxidation 50 ml water are added to the crude reaction mixture. 4.46 g of hydrogen peroxide (30% in $H_2O$, 40.5 mmol) are added within 5 min at room temperature. After heating to 50-60° C. stirring is continued for 2 h. The reaction mixture is separated and the organic layer is extracted with 2% aqueous $NaHCO_3$ and saturated NaCl solution, followed by drying over $Na2SO_4$ and concentration under vacuum. The crude 10.6 g yellow oil is purified by prep-chromatography (heptane/ethylacetate 20:80; silicagel), resulting in 0.87 g acetic acid 3-[bis-(2,6-dichloro-benzoyl)-phosphinoyl]-propyl ester as yellow crystals (yield 7%).

$^{31}$P-NMR ($CDCl_3$): 25.0 ppm

Example 38 (Table 3) is prepared using the same reaction sequence as for sample B, expect that in step d the alkylating agent listed in Table 3 is used instead of 3-bromopropylacetate.

TABLE 3

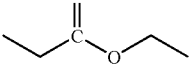

| Ex. | alkylating agent | $R_1$ | $^{31}$P-NMR ($C_6D_6$) ppm | $^{31}$P-NMR ($CDCl_3$) ppm | yield | mp [° C.] |
|---|---|---|---|---|---|---|
| 38 | ethyl chloroacetate | (structure) | 37.9 | 15.2 | 35%[a] | 92-95 |

[a] after crystallisation from hexane

Example 39 and 40

Examples 39 and 40 (Table 4) are prepared using the same reaction sequence as described for example 1, expect that in step d the alkylating agent listed in Table 4 is used instead of isobutyl bromide.

TABLE 4

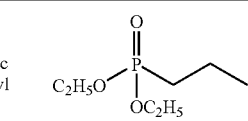

| Ex. | alkylating agent | $R_1$ | $^{31}$P-NMR ($C_6D_6$) ppm | $^{31}$P-NMR ($CDCl_3$) ppm | yield | mp [° C.] |
|---|---|---|---|---|---|---|
| 39 | (2-bromo-ethyl)-phosphonic acid diethyl ester | $C_2H_5O-P(=O)(OC_2H_5)-$ | 55.6 | 24.5 | 50% | resin |
| 40 | 5-bromo-methyl-bicyclo[2.2.1]-hept-2-ene[1] | (structure) | 50.4 | 28.5 | 24% | wax |

[1] mixture of endo and exo stereoisomer

Example 41

Preparation of [Bis-(2-ethoxy-naphthalene-1-carbonyl)-phosphinoyl]-acetic acid ethyl ester, starting from phosphorus trichloride

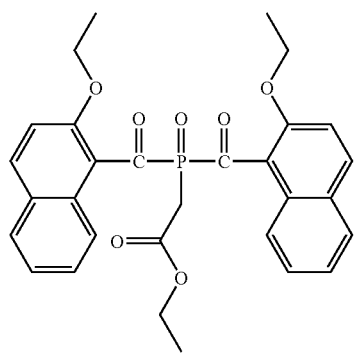

The compound of example 41 is prepared following the reaction sequence of example 32, except that 2-ethoxy-naphthalene-1-carbonyl chloride is used for the acylation step 15c and ethyl 2-bromoacetate in the alkylation step 15d). [Bis-(2-ethoxy-naphthalene-1-carbonyl)-phosphanyl]-acetic acid ethyl ester obtained in step d) has a $^{31}$P-NMR resonance at 51.77 ppm.

Examples 42-75

Preparation of 2-[bis-(2,4,6-trimethyl-benzoyl)-phosphanyl]acetic acid esters and 2-[bis-(2,4,6-trimethyl-benzoyl)-phosphinoyl]acetic acid esters The 2-[bis-(2,4,6-trimethyl-benzoyl)-phosphanyl]acetic acid esters (Formula A) and 2-[bis-(2,4,6-trimethyl-benzoyl)-phosphinoyl]acetic acid esters (Formula B) derivatives of examples 42-75 (Table 5) are prepared using the reaction sequence reported for Example 15, expect that in step d the alkylating agents listed in Table 5 are used instead of 3-bromopropylacetate.

TABLE 5

A
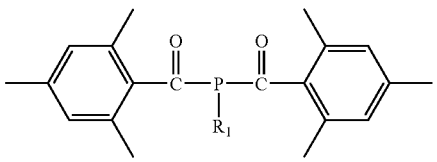

B
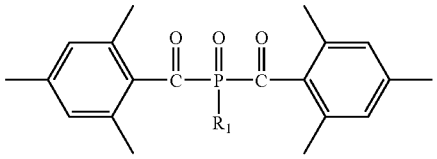

| Ex | Alkylating agent | R₁ | Chemical name of bisacylphosphine oxide |
|----|------------------|-----|------------------------------------------|
| 42 | propyl 2-bromoacetate | —CH₂—C(=O)—O—CH₂CH₂CH₃ | [Bis-(2,4,6-trimethyl-benzoyl)-phosphinoyl]-acetic acid propyl ester |
| 43 | isopropyl 2-bromo-acetate | —CH₂—C(=O)—O—CH(CH₃)₂ | [[Bis-(2,4,6-trimethyl-benzoyl)-phosphinoyl]-acetic acid isopropyl ester |
| 44 | n-butyl 2-chlorocetate | —CH₂—C(=O)—O—CH₂CH₂CH₂CH₃ | [[Bis-(2,4,6-trimethyl-benzoyl)-phosphinoyl]-acetic acid butyl ester |
| 45 | isobutyl 2-chloro-acetate | —CH₂—C(=O)—O—CH₂CH(CH₃)₂ | [Bis-(2,4,6-trimethyl-benzoyl)-phosphinoyl]-acetic acid isobutyl ester |
| 46 | pentyl 2-chloroacetate | —CH₂—C(=O)—O—CH₂CH₂CH₂CH₂CH₃ | [Bis-(2,4,6-trimethyl-benzoyl)-phosphinoyl]-acetic acid pentyl ester |

TABLE 5-continued

A

B

| Ex | Alkylating agent | R₁ | Chemical name of bisacylphosphine oxide |
|---|---|---|---|
| 47 | 3-methylbutyl 2-chloroacetate | —CH₂—C(=O)—O—CH₂CH₂CH(CH₃)₂ | [Bis-(2,4,6-trimethyl-benzoyl)-phosphinoyl]-acetic acid 3-methyl-butyl ester |
| 48 | cyclohexyl 2-chloro-acetate | —CH₂—C(=O)—O—cyclohexyl | [[Bis-(2,4,6-trimethyl-benzoyl)-phosphinoyl]-acetic acid cyclohexyl ester |
| 49 | hexyl 2-chloro-acetate | —CH₂—C(=O)—O—(CH₂)₅CH₃ | [[Bis-(2,4,6-trimethyl-benzoyl)-phosphinoyl]-acetic acid hexyl ester |
| 49B | 2-ethylbutyl 2-chloroacetate | —CH₂—C(=O)—O—CH₂CH(C₂H₅)C₂H₅ | Bis-(2,4,6-trimethyl-benzoyl)-phosphinoyl]-acetic acid 2-ethyl-butyl ester |
| 50 | heptyl 2-chloroacetate | —CH₂—C(=O)—O—(CH₂)₆CH₃ | [Bis-(2,4,6-trimethyl-benzoyl)-phosphinoyl]-acetic acid heptyl ester |
| 51 | 2-ethylhexyl 2-chloroacetate | —CH₂—C(=O)—O—CH₂CH(C₂H₅)(CH₂)₃CH₃ | [Bis-(2,4,6-trimethyl-benzoyl)-phosphinoyl]-acetic acid 2-ethyl-hexyl ester |
| 52 | n-octyl 2-chloroacetate | —CH₂—C(=O)—O—(CH₂)₇CH₃ | [Bis-(2,4,6-trimethyl-benzoyl)-phosphinoyl]-acetic acid octyl ester |
| 53 | n-decyl 2-bromo-acetate | —CH₂—C(=O)—O—(CH₂)₉CH₃ | [Bis-(2,4,6-trimethyl-benzoyl)-phosphinoyl]-acetic acid decyl ester |
| 54 | 3,7-dimethyl-octyl 2-chloroacetate | —CH₂—C(=O)—O—CH₂CH₂CH(CH₃)(CH₂)₃CH(CH₃)₂ | [Bis-(2,4,6-trimethyl-benzoyl)-phosphinoyl]-acetic acid 3,7-dimethyl-octyl ester |

TABLE 5-continued

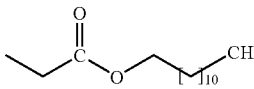

A

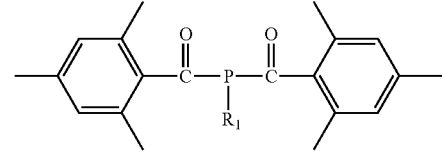

B

| Ex | Alkylating agent | R₁ | Chemical name of bisacylphosphine oxide |
|---|---|---|---|
| 55 | n-dodecyl 2-chloro-acetate | 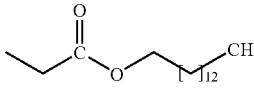 | [[Bis-(2,4,6-trimethyl-benzoyl)-phosphinoyl]-acetic acid dodecyl ester |
| 56 | n-tetradecyl 2-chloro-acetate | 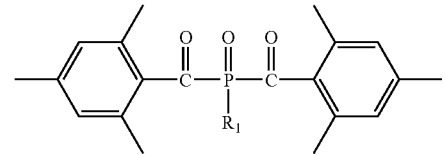 | [[Bis-(2,4,6-trimethyl-benzoyl)-phosphinoyl]-acetic acid tetradecyl ester |
| 57 | n-hexadecyl 2-chloro-acetate | 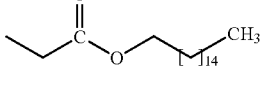 | [Bis-(2,4,6-trimethyl-benzoyl)-phosphinoyl]-acetic acid hexadecyl ester |
| 58 | 3-phenylpropyl 2-chloroacetate | 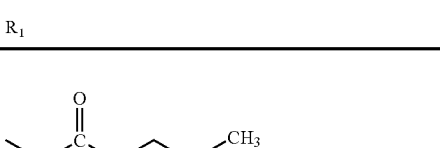 | [Bis-(2,4,6-trimethyl-benzoyl)-phosphinoyl]-acetic acid 3-phenyl-propyl ester |
| 59 | 2-propenyl 2-chloroacetate | 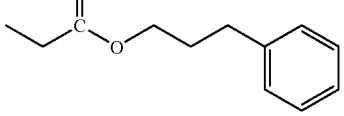 | [Bis-(2,4,6-trimethyl-benzoyl)-phosphinoyl]-acetic acid allyl ester |
| 60 | 3-phenylallyl 2-chloroacetate | 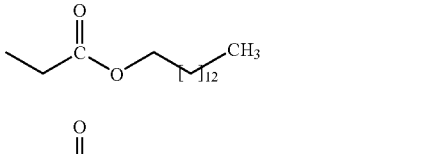 | [Bis-(2,4,6-trimethyl-benzoyl)-phosphinoyl]-acetic acid (E)-3-phenyl-allyl ester |
| 61 | 2-chloroethyl 2-chloroacetate | 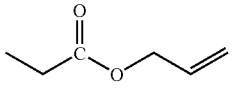 | [Bis-(2,4,6-trimethyl-benzoyl)-phosphinoyl]-acetic acid 2-chloro-ethyl ester |
| 62 | 2-methoxyethyl 2-chloroacetate | 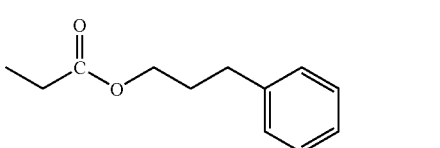 | [Bis-(2,4,6-trimethyl-benzoyl)-phosphinoyl]-acetic acid 2-methoxy-ethyl ester |
| 63 | 2-(2-methoxy-ethoxy)-ethyl 2-chloroacetate | 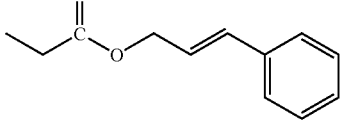 | [Bis-(2,4,6-trimethyl-benzoyl)-phosphinoyl]-acetic acid 2-(2-methoxy-ethoxy)-ethyl ester |

TABLE 5-continued

A

B

| Ex | Alkylating agent | R₁ | Chemical name of bisacylphosphine oxide |
|---|---|---|---|
| 64 | 2-(2-ethoxyethoxy)-ethyl 2-chloroacetate | –CH₂–C(=O)–O–CH₂CH₂–O–CH₂CH₂–O–CH₂CH₃ | [Bis-(2,4,6-trimethyl-benzoyl)-phosphinoyl]-acetic acid 2-(2-ethoxy-ethoxy)-ethyl ester |
| 65 | 2-[2-(butoxy)ethoxy]-ethyl 2-bromoacetate | –CH₂–C(=O)–O–CH₂CH₂–O–CH₂CH₂–O–C₄H₉ | [Bis-(2,4,6-trimethyl-benzoyl)-phosphinoyl]-acetic acid 2-(2-butoxy-ethoxy)-ethyl ester |
| 66 | 2-[2-(hexyloxy)ethoxy]-ethyl 2-bromoacetate | –CH₂–C(=O)–O–CH₂CH₂–O–CH₂CH₂–O–C₆H₁₃ | [Bis-(2,4,6-trimethyl-benzoyl)-phosphinoyl]-acetic acid 2-(2-hexyloxy-ethoxy)-ethyl ester |
| 67 | 2-[2-(2-methoxy-ethoxy)ethoxy]-ethyl 2-chloroacetate | –CH₂–C(=O)–O–CH₂CH₂–O–CH₂CH₂–O–CH₂CH₂–O–CH₃ | [Bis-(2,4,6-trimethyl-benzoyl)-phosphinoyl]-acetic acid 2-[2-(2-methoxy-ethoxy)-ethoxy]-ethyl ester |
| 68 | 2-[2-(2-ethoxyethoxy)-ethoxy]ethyl 2-bromo-acetate | –CH₂–C(=O)–O–CH₂CH₂–[O–CH₂CH₂]₂–O–CH₂CH₃ | [Bis-(2,4,6-trimethyl-benzoyl)-phosphinoyl]-acetic acid 2-[2-(2-ethoxy-ethoxy)-ethoxy]-ethyl ester |
| 69 | 3,6,9,12-tetraoxa-tridec-1-yl 2-bromo-acetate | –CH₂–C(=O)–O–CH₂CH₂–[O–CH₂CH₂]₃–O–CH₃ | [Bis-(2,4,6-trimethyl-benzoyl)-phosphinoyl]-acetic acid 2-{2-[2-(2-methoxy-ethoxy)-ethoxy]-ethoxy}-ethyl ester[Bis-(2,4,6-trimethyl-benzoyl)-phosphinoyl]-acetic acid 2-(2-{2-[2-(2-methoxy-ethoxy)-ethoxy]-ethoxy}-ethoxy)-ethyl ester |
| 70 | 3-cyclohexyl-propyl 2-chloroacetate | –CH₂–C(=O)–O–CH₂CH₂CH₂–C₆H₁₁ | [Bis-(2,4,6-trimethyl-benzoyl)-phosphinoyl]-acetic acid 3-cyclohexyl-propyl ester |

TABLE 5-continued

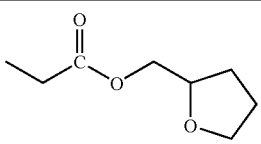

A

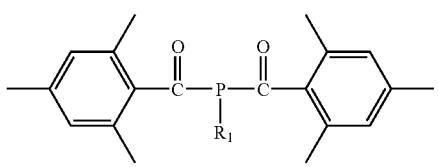

B

| Ex | Alkylating agent | R₁ | | Chemical name of bisacylphosphine oxide |
|----|------------------|----|----|----------------------------------------|
| 71 | tetrahydro-furan-2-yl-methyl 2-chloroacetate | 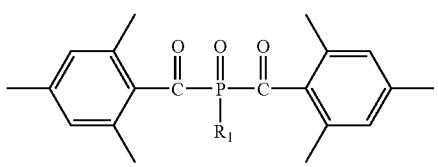 | | [Bis-(2,4,6-trimethyl-benzoyl)-phosphinoyl]-acetic acid tetrahydro-furan-2-yl ester |
| 72 | 2-isopropyl-5-methyl-cyclohexyl-2-chloroacetate | 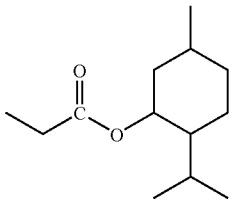 | | [Bis-(2,4,6-trimethyl-benzoyl)-phosphinoyl]-acetic acid 2-isopropyl-4-methyl-cyclohexyl ester |
| 73 | benzyl 2-brormoacetate | 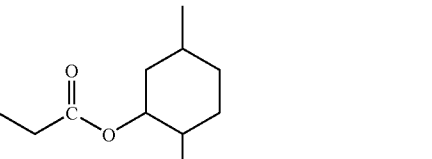 | | [Bis-(2,4,6-trimethyl-benzoyl)-phosphinoyl]-acetic acid benzyl ester |
| 74 | 2-furanylmethyl 2-chloroacetate | 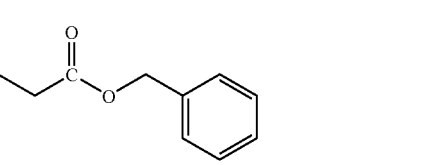 | | [Bis-(2,4,6-trimethyl-benzoyl)-phosphinoyl]-acetic acid furan-2-ylmethyl ester |
| 75 | phenyl 2-brormacetate | 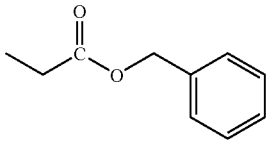 | | [Bis-(2,4,6-trimethyl-benzoyl)-phosphinoyl]-acetic acid phenyl ester |

Alternatively, the compounds collected in Table 5 can also be prepared by transesterification of the methyl ester (Example 17) or ethyl ester (Example 18) with the corresponding alcohol in the presence of a suitable catalyst using reaction conditions known to in the literature. Suitable catalyst are, for example but without limiting to these examples, tin oxide, Fascat 4200 (dibutylzinn-diacetate commercially available of the Arkema group), aluminium(III) acetylacetonate or zirconium(IV) propoxide.

Examples 76-78

Preparation of 2-[bis-(2,4,6-trimethyl-benzoyl)-phosphanyl]acetic acid esters and 2-[bis-(2,4,6-trimethyl-benzoyl)-phosphinoyl]acetic acid esters The 2-[bis-(2,4,6-trimethyl-benzoyl)-phosphanyl]acetic acid esters (Formula A) and 2[bis-(2,4,6-trimethyl-benzoyl)-phosphinoyl]acetic acid esters (Formula B) derivatives of examples 76-78 (Table 6) are by transesterification of the methyl ester (Example 17) using the alcohol listed in Table 6 alcohol in the presence of Fascat 4200, as catalyst.

TABLE 6

A: Structure showing bis(2,4,6-trimethylbenzoyl) group attached to P with R$_1$ substituent (phosphine form)

B: Structure showing bis(2,4,6-trimethylbenzoyl) group attached to P=O with R$_1$ substituent (phosphine oxide form)

| Ex. | alcohol | R$_1$ | Chemical name of bisacylphosphine oxide |
|---|---|---|---|
| 76 | diethylene glycol | HO-CH$_2$CH$_2$-O-CH$_2$CH$_2$-OH | [Bis-(2,4,6-trimethyl-benzoyl)-phosphinoyl]-acetic acid 2-(2-hydroxy-ethoxy)-ethyl ester |
| 77 | triethylene glycol | HO-CH$_2$CH$_2$-O-CH$_2$CH$_2$-O-CH$_2$CH$_2$-OH | [Bis-(2,4,6-trimethyl-benzoyl)-phosphinoyl]-acetic acid 2-[2-(2-hydroxy-ethoxy)-ethoxy]-ethyl ester |
| 78 | tetraethylene glycol | HO-CH$_2$CH$_2$-O-CH$_2$CH$_2$-O-CH$_2$CH$_2$-O-CH$_2$CH$_2$-OH | [Bis-(2,4,6-trimethyl-benzoyl)-phosphinoyl]-acetic acid 2-{2-[2-(2-hydroxy-ethoxy)-ethoxy]-ethoxy}-ethyl ester |

Examples 79-80

Preparation of 1-[bis-(2,4,6-trimethyl-benzoyl)-phosphanyl]-alkanes and 1-[bis-(2,4,6-trimethyl-benzoyl)-phosphinoyl]-alkanes 1-[Bis-(2,4,6-trimethyl-benzoyl)-phosphanyl]-alkanes (Formula A) and 1-[bis-(2,4,6-trimethyl-benzoyl)-phosphinoyl]-alkanes (Formula B) of Examples 79-80 (Table 7) are prepared using the same reaction sequence as described for example 1, expect that in step d the alkylating agent listed in Table 4 is used instead of isobutyl bromide.

TABLE 7

A: Structure showing bis(2,4,6-trimethylbenzoyl) group attached to P with R$_1$ substituent (phosphanyl form)

B: Structure showing bis(2,4,6-trimethylbenzoyl) group attached to P=O with R$_1$ substituent (phosphinoyl form)

| Ex. | alkylating agent | R$_1$ | Chemical name of bisacylphosphine oxide |
|---|---|---|---|
| 79 | 1-bromo-butan | butyl chain | [Butyl-(2,4,6-trimethyl-benzoyl)-phosphinoyl]-(2,4-dimethyl-phenyl)-methanone |

TABLE 7-continued

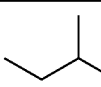

| Ex. | alkylating agent | $R_1$ | Chemical name of bisacylphosphine oxide |
|---|---|---|---|
| 80 | 1-bromo-2,4,4-trimethyl-pentan | | (2,4-Dimethyl-phenyl)-[(2,4,6-trimethyl-benzoyl)-(2,4,4-trimethyl-pentyl)-phosphinoyl]-methanone |

Examples 81-86

Preparation of 1-[bis-(2,4,6-trimethyl-benzoyl)-phosphanyl]-pentane-2,4-dione and 1-[bis-(2,4,6-trimethyl-benzoyl)-phosphinoyl]-pentane-2,4-dione derivatives or 4-[bis-(2,4,6-trimethyl-benzoyl)-phosphanyl]-3-oxo-butyric acid esters 4-[bis-(2,4,6-trimethyl-benzoyl)-phosphinoyl]-3-oxo-butyric acid esters The bis-(2,4,6-trimethyl-benzoyl)-phosphanyl (Formula A) and bis-(2,4,6-trimethyl-benzoyl)-phosphinoyl derivatives (Formula B) of examples 81-86 (Table 8) are prepared using the reaction sequence reported for example 15, expect that in step d the alkylating agents listed in Table 7 are used instead of 3-bromopropylacetate.

TABLE 8

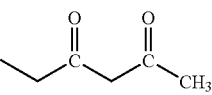

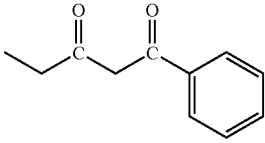

| Ex. | alkylating agent | $R_1$ | Chemical name of bisacylphosphine oxide |
|---|---|---|---|
| 81 | 1-chloro-2,4-pentanedione | | 1-[Bis-(2,4,6-trimethyl-benzoyl)-phosphinoyl]-pentane-2,4-dione |
| 82 | 4-bromo-1-phenyl-1,3-butanedione | | 4-[Bis-(2,4,6-trimethyl-benzoyl)-phosphinoyl]-1-phenyl-butane-1,3-dione |

TABLE 8-continued

A

B

| Ex. | alkylating agent | R$_1$ | Chemical name of bisacylphosphine oxide |
|---|---|---|---|
| 83 | methyl 4-chloro-3-oxo-butanoate | (structure: CH$_3$CH$_2$-C(=O)-CH$_2$-C(=O)-O-CH$_3$) | 4-[Bis-(2,4,6-trimethyl-benzoyl)-phosphinoyl]-3-oxo-butyric acid methyl ester |
| 84 | ethyl 4-chloro-3-oxo-butanoate | (structure: CH$_3$CH$_2$-C(=O)-CH$_2$-C(=O)-O-CH$_2$CH$_3$) | 4-[Bis-(2,4,6-trimethyl-benzoyl)-phosphinoyl]-3-oxo-butyric acid ethyl ester |
| 85 | 1-methylethyl 4-chloro-3-oxo-butanoate | (structure: CH$_3$CH$_2$-C(=O)-CH$_2$-C(=O)-O-CH(CH$_3$)$_2$) | 4-[Bis-(2,4,6-trimethyl-benzoyl)-phosphinoyl]-3-oxo-butyric acid isopropyl ester |
| 86 | octyl 4-chloro-3-oxo-butanoate | (structure: CH$_3$CH$_2$-C(=O)-CH$_2$-C(=O)-O-(CH$_2$)$_7$CH$_3$) | 4-[Bis-(2,4,6-trimethyl-benzoyl)-phosphinoyl]-3-oxo-butyric acid octyl ester |

Examples 87-93

Preparation of [bis-(2-ethoxy-naphthalene-1-carbonyl)-phosphanyl]-acetic acid ester derivatives and [bis-(2-ethoxy-naphthalene-1-carbonyl)-phosphinoyl]-acetic acid ester derivatives The [bis-(2-ethoxy-naphthalene-1-carbonyl)-phosphanyl]-acetic acid ester derivatives (Formula A) and [bis-(2-ethoxy-naphthalene-1-carbonyl)-phosphinoyl]-acetic acid ester derivatives (Formula B) of examples 87-93 are prepared following the reaction sequence of example 41, except that that in step d the alkylating agents listed in Table 9 are used instead of 3-bromopropylacetate

TABLE 9

A: (structure showing bisacylphosphine with two 2-ethoxy-naphthalenyl carbonyl groups attached to P-R₁)

B: (structure showing bisacylphosphine oxide with two 2-ethoxy-naphthalenyl carbonyl groups attached to P(=O)-R₁)

| Ex. | alkylating agent | R₁ | Chemical name of bisacylphosphine oxide |
|---|---|---|---|
| 87 | hexyl 2-chloro-acetate | –CH₂–C(=O)–O–(CH₂)₅CH₃ | [[Bis-(2,4,6-trimethyl-benzoyl)-phosphinoyl]-acetic acid hexyl ester |
| 88 | 2-ethylhexyl 2-chloroacetate | –CH₂–C(=O)–O–CH₂CH(C₂H₅)(CH₂)₃CH₃ | [Bis-(2,4,6-trimethyl-benzoyl)-phosphinoyl]-acetic acid 2-ethyl-hexyl ester |
| 89 | n-decyl 2-bromo-acetate | –CH₂–C(=O)–O–(CH₂)₉CH₃ | [Bis-(2,4,6-trimethyl-benzoyl)-phosphinoyl]-acetic acid decyl ester |
| 90 | n-tetradecyl 2-chloro-acetate | –CH₂–C(=O)–O–CH₂–(CH₂)₁₂–CH₃ | [[Bis-(2,4,6-trimethyl-benzoyl)-phosphinoyl]-acetic acid tetradecyl ester |
| 91 | 2-(2-methoxy-ethoxy)-ethyl 2-chloroacetate | –CH₂–C(=O)–O–CH₂CH₂–O–CH₂CH₂–O–CH₃ | [Bis-(2,4,6-trimethyl-benzoyl)-phosphinoyl]-acetic acid 2-(2-methoxy-ethoxy)-ethyl ester |
| 92 | 2-(2-ethoxy-ethoxy)-ethyl 2-chloroacetate | –CH₂–C(=O)–O–CH₂CH₂–O–CH₂CH₂–O–C₂H₅ | [Bis-(2,4,6-trimethyl-benzoyl)-phosphinoyl]-acetic acid 2-(2-ethoxy-ethoxy)-ethyl ester |
| 93 | 2-[2-(2-methoxy-ethoxy)ethoxy]-ethyl 2-chloroacetate | –CH₂–C(=O)–O–CH₂CH₂–O–CH₂CH₂–O–CH₂CH₂–O–CH₃ | [Bis-(2,4,6-trimethyl-benzoyl)-phosphinoyl]-acetic acid 2-[2-(2-methoxy-ethoxy)-ethoxy]-ethyl ester |

Alternatively, the compounds collected in Table 9 can also be prepared by transesterification of the ethyl ester (Example 41) with the corresponding alcohol in the presence of a suitable catalyst using reaction conditions known in the literature. Suitable catalyst are, for example but without limiting to these examples, tin oxide, Fascat 4200 (Arkema Group), aluminium(III) acetylacetonate or zirconium(IV) propoxide.

Examples 94-100

Preparation of [(2-ethoxy-naphthalene-1-carbonyl)-(2,4,6-trimethylbenzoyl)-phosphanyl]-acetic acid ester derivatives and [(2-ethoxy-naphthalene-1-carbonyl)-(2,4,6-trimethylbenzoyl)-phosphionoyl]-acetic acid ester derivatives The [(2-ethoxy-naphthalene-1-carbonyl)-(2,4,6-trimethylbenzoyl)-phosphanyl]-acetic acid ester derivatives and [(2-ethoxy-naphthalene-1-carbonyl)-(2,4,6-trimethylbenzoyl)-phosphionoyl]-acetic acid ester derivatives of examples 94-100 are prepared following the reaction sequence of example 14, except that [(2-ethoxy-naphthalene-1-carboxylic acid chloride is used in the first acylation step instead of pivaloyl chloride and the alkylating agents listed in Table 10 are used instead of methyl iodide.

TABLE 10

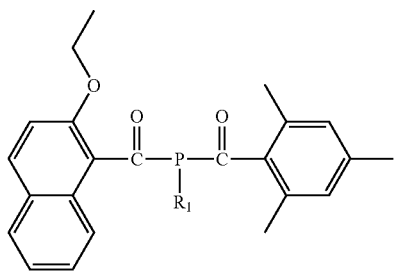

A

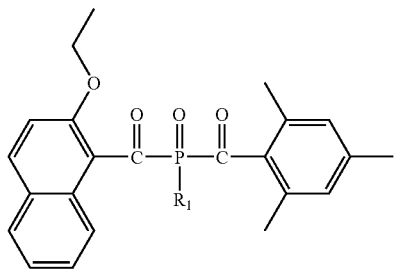

B

| Ex. | alkylating agent | $R_1$ | Chemical name of bisacylphosphine oxide |
|---|---|---|---|
| 94 | hexyl 2-chloro-acetate | ![structure] | [[Bis-(2,4,6-trimethyl-benzoyl)-phosphinoyl]-acetic acid hexyl ester |
| 95 | 2-ethylhexyl 2-chloroacetate | ![structure] | [Bis-(2,4,6-trimethyl-benzoyl)-phosphinoyl]-acetic acid 2-ethylhexyl ester |
| 96 | n-decyl 2-bromo-acetate | ![structure] | [Bis-(2,4,6-trimethyl-benzoyl)-phosphinoyl]-acetic acid decyl ester |

TABLE 10-continued

A

B

| Ex. | alkylating agent | R₁ | Chemical name of bisacylphosphine oxide |
|---|---|---|---|
| 97 | n-tetradecyl 2-chloro-acetate | -CH₂-C(=O)-O-(CH₂)₁₂-CH₃ | [[Bis-(2,4,6-trimethyl-benzoyl)-phosphinoyl]-acetic acid tetradecyl ester |
| 98 | 2-(2-methoxy-ethoxy)-ethyl 2-chloro-acetate | -CH₂-C(=O)-O-CH₂CH₂-O-CH₂CH₂-O-CH₃ | [Bis-(2,4,6-trimethyl-benzoyl)-phosphinoyl]-acetic acid 2-(2-methoxy-ethoxy)-ethyl ester |
| 99 | 2-(2-ethoxyethoxy)-ethyl 2-chloroacetate | -CH₂-C(=O)-O-CH₂CH₂-O-CH₂CH₂-O-CH₂CH₃ | [Bis-(2,4,6-trimethyl-benzoyl)-phosphinoyl]-acetic acid 2-(2-ethoxy-ethoxy)-ethyl ester |
| 100 | 2-[2-(2-methoxy-ethoxy)ethoxy] ethyl 2-chloro-acetate | -CH₂-C(=O)-O-CH₂CH₂-O-CH₂CH₂-O-CH₂CH₂-O-CH₃ | [Bis-(2,4,6-trimethyl-benzoyl)-phosphinoyl]-acetic acid 2-[2-(2-methoxy-ethoxy)-ethoxy]-ethyl ester |

Alternatively, the compounds collected in Table 10 can also be prepared by transesterification of the ethyl ester (Example 41) with the corresponding alcohol in the presence of a suitable catalyst using reaction conditions known in the literature. Suitable catalyst are, for example but without limiting to these examples, tin oxide, Fascat 4200 (Arkema Group), aluminium(III) acetylacetonate or zirconium(IV) propoxide.

Examples 101-106

Preparation of diesters of bis-(2,4,6-trimethyl-benzoyl)-phosphanoyl]-acetic acid and bis-(2,4,6-trimethyl-benzoyl)-phosphinoyl]-acetic acid The diesters of bis-(2,4,6-trimethyl-benzoyl)-phosphanoyl]-acetic acid (Formula A) and bis-(2,4,6-trimethyl-benzoyl)-phosphinoyl]-acetic acid (Formula B) derivatives of examples 101-106 (Table 11) are prepared using the reaction sequence reported for example 15, expect that in step d the 0.5 equivalents of the alkylating agents listed in Table 11 are used instead of 3-bromopropylacetate.

TABLE 11

A

B

| Ex. | alkylating agent | R₁ | Chemical name of bisacylphosphine oxide |
|---|---|---|---|
| 101 | Chloro-acetic acid 2-(2-chloro-acetoxy)-ethyl ester | | [(2,4-Dimethyl-benzoyl)-(2,4,6-trimethyl-benzoyl)-phosphinoyl]-acetic acid 2-{2-[bis-(2,4,6-trimethyl-benzoyl)-phosphinoyl]-acetoxy}-ethyl ester |
| 102 | Chloro-acetic acid 3-(2-chloro-acetoxy)-propyl ester | | [Bis-(2,4,6-trimethyl-benzoyl)-phosphinoyl]-acetic acid 3-{2-[(2,4-dimethyl-benzoyl)-(2,4,6-trimethy-benzoyl)-phosphinoyl]-acetoxy}-propyl ester |
| 103 | Chloro-acetic acid 5-(2-chloro-acetoxy)-pentyl ester | | [Bis-(2,4,6-trimethyl-benzoyl)-phosphinoyl]-acetic acid 5-{2-[(2,4-dimethyl-benzoyl)-(2,4,6-trimethyl-benzoyl)-phosphinoyl]-acetoxy}-pentyl ester |
| 104 | Chloro-acetic acid 2-[2-(2-chloro-acetoxy)-ethoxy]-ethyl ester | | [Bis-(2,4,6-trimethyl-benzoyl)-phosphinoyl]-acetic acid 2-(2-{2-[(2,4-dimethyl-benzoyl)-(2,4,6-trimethyl-benzoyl)-phosphinoyl]-acetoxy}-ethoxy)-ethyl ester |

TABLE 11-continued

A

B

| Ex. | alkylating agent | $R_1$ | Chemical name of bisacylphosphine oxide |
|---|---|---|---|
| 105 | Chloro-acetic acid 2-{2-[2-(2-chloro-acetoxy)-ethoxy]-ethoxy}-ethyl ester | | [Bis-(2,4,6-trimethyl-benzoyl)-phosphinoyl]-acetic acid 2-[2-(2-{2-[(2,4-dimethyl-benzoyl)-(2,4,6-trimethyl-benzoyl)-phosphinoyl]-acetoxy}-ethoxy)-ethoxy]-ethyl ester |
| 106 | Chloro-acetic acid 2-(2-{2-[2-(2-chloro-acetoxy)-ethoxy]-ethoxy}-ethoxy)-ethyl ester | | [Bis-(2,4,6-trimethyl-benzoyl)-phosphinoyl]-acetic acid 2-{2-[2-(2-{2-[(2,4-dimethyl-benzoyl)-(2,4,6-trimethyl-benzoyl)-phosphinoyl]-acetoxy}-ethoxy)-ethoxy]-ethoxy}-ethyl ester |

Alternatively, the compounds collected in Table 11 can also be prepared by transesterification of the methyl ester (Example 17) or ethyl ester (Example 18) with 0.5 equivalents of the corresponding alcohol in the presence of a suitable catalyst using reaction conditions known in the literature. Suitable catalyst are, for example but without limiting to these examples, tin oxide, Fascat 4200 (Arkema Group), aluminium(III) acetylacetonate or zirconium(IV)propoxide.

Application Examples

Pendulum Hardness

A UV-curable white coat is prepared by mixing
67.5 parts of polyester acrylate oligomer (®EBECRYL 830, UCB, Belgium)
5.0 parts of hexanediol diacrylate
2.5 parts of trimethylolpropane triacrylate
25.0 parts of rutile titanium dioxide (®R-TC2, Tioxide, France)
2.0 parts of the photoinitiator The coating is applied to a coil-coated aluminium sheet using a 100 m slotted doctor knife and then cured. Curing is carried out by conveying the sample twice, on a conveyor belt which is moving at a speed of 10 m/min, beneath an 80 W/cm medium-pressure mercury lamp (Hanovia, USA). The pendulum hardness is then determined in accordance with König (DIN53157) in [s]. The pendulum hardness is a measure of the through-curing of the composition. The higher the values, the more effective the curing which has been carried out. After the first pendulum hardness determination, the sample is after-exposed under low-pressure mercury lamps of the type TL 40W/03 (Philips; Emission maximum of 430 nm), and after 16 h the pendulum hardness is determined again.

Yellow Index

The yellow Index b was determined in accordance with ASTMD 1925-88.

The Table below shows the results.

| Photo-initiator | Pendulum hardness | | Yellow index | |
| --- | --- | --- | --- | --- |
| | direct after curing | after 16 h after expose | direct after curing | after 16 h after expose |
| Ex. 10 (Irgacure 819) | 171 | 203 | 3.9 | 1.5 |
| Ex. 3 | 167 | 202 | 3.9 | 1.5 |
| Ex. 14 | 172 | 202 | 3.4 | 1.5 |
| Ex. 18 | 165 | 199 | 3.9 | 1.6 |
| Ex. 19 | 175 | 196 | 3.9 | 1.6 |
| Ex. 21 | 162 | 196 | 3.8 | 1.6 |
| Ex. 24 | 157 | 196 | 4.0 | 1.6 |
| Ex. 26 | 165 | 196 | 3.7 | 1.6 |
| Ex. 37 | 155 | 189 | 3.6 | 2.1 |
| Ex. 39 | 178 | 200 | 3.9 | 1.5 |

The invention claimed is:

1. A process for the preparation of acylphosphanes or bisacylphosphanes of formula I

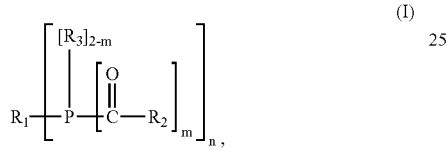

wherein n and m are each independently of the other 1 or 2;

$R_1$ if n=1, is unsubstituted linear or branched $C_1$-$C_{18}$alkyl or $C_2$-$C_{18}$alkenyl; or linear or branched $C_1$-$C_{18}$alkyl or $C_2$-$C_{18}$alkenyl substituted once or more than once by groups selected from: halogen or CN, or

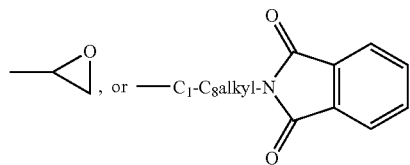

—$OR_{10}$, —$SR_{10}$, —OCO—$R_{10}$, —COO—$R_{10}$, —CH=CH—CO—$OR_{10}$ or —C($C_1$-$C_4$alkyl)=C($C_1$-$C_4$alkyl)-CO—$OR_{10}$; wherein $R_{10}$ is hydrogen, $C_1$-$C_{18}$alkyl, or $C_2$-$C_{18}$alkyl which is interrupted by one or several non-successive —O-atoms, a di-,tri,-tetra-or polyethylene glycol residue, $C_3$-$C_{12}$-cycloalkyl, tetrahydropyran-2-yl, phenyl-$C_1$-$C_4$-alkylene, phenyl-$C_1$-$C_4$-alkenylene, $C_1$-$C_6$alkyl substituted by halogen or substituted by cyclohexyl or cyclopentyl, or substituted by tetrahydrofuranyl, furanyl, isopropyl-4-methyl-coclohexyl, $C_2$-$C_{18}$-alkenyl, unsubstituted phenyl, naphthyl or biphenyl being unsubstituted or phenyl, naphthyl or biphenyl substituted by one to five $C_1$-$C_8$-alkyl, $C_1$-$C_8$-alkoxy, $C_1$-$C_8$-alkylthio and/or halogen; or $R_1$ is linear or branched $C_1$-$C_{18}$alkyl or $C_2$-$C_{18}$alkenyl substituted by —CO—$R_{11}$; wherein $R_{11}$ is $C_1$-$C_{18}$alkyl, or $C_2$-$C_{18}$alkyl which is interrupted by one or several non-successive —O-atoms, $C_3$-$C_{12}$-cycloalkyl, phenyl-$C_1$-$C_4$-alkylene, unsubstituted phenyl, naphthyl or biphenyl being unsubstituted or phenyl, naphthyl or biphenyl substituted by one to five $C_1$-$C_8$-alkyl, $C_1$-$C_8$-alkoxy, $C_1$-$C_8$-alkylthio and/or halogen or $R_1$ is linear or branched $C_1$-$C_{18}$alkyl or $C_2$-$C_{18}$alkenyl substituted by —CO—($CH_2$)$_2$—CO—$C_1$-$C_6$alkyl, CO—($CH_2$)$_2$—CO-phenyl, or by CO—($CH_2$)$_2$—COO—$C_1$-$C_{18}$alkyl; or $R_1$ is linear or branched $C_1$-$C_{18}$alkyl or $C_2$-$C_{18}$alkenyl substituted by —$NR_{12}R_{13}$, —$N(R_{12})$—CO—$R_{10}$, —$N(R_{12})$—CO—$OR_{10}$, —$N(R_{12})$—CO—$NR_{12}R_{13}$, —$N(R_{12})$—CO-Hal, —CO—$NR_{12}R_{13}$, wherein $R_{10}$ is as defined above and $R_{12}$ and $R_{13}$ independently of one another are hydrogen, $C_1$-$C_{18}$alkyl, $C_2$-$C_{18}$alkyl which is interrupted by one or several non-successive O atoms, $C_3$-$C_{12}$-cycloalkyl, $C_2$-$C_{18}$-alkenyl, phenyl-$C_1$-$C_4$-alkyl, phenyl, naphthyl, pyridyl, the radicals phenyl, naphthyl or pyridyl being unsubstituted or substituted by one to five $C_1$-$C_8$-alkyl, $C_1$-$C_8$-alkoxy, $C_1$-$C_8$-alkylthio and/or halogen; or $R_{12}$ and $R_{13}$ forms a 5- or 6-membered O-, S- or N-containing heterocyclic ring; that may be further annelated by an aliphatic or aromatic ring; or —$SO_2$—$R_{10}$, —$SO_2$—$OR_{10}$, —$SO_2$—$NR_{12}R_{13}$, wherein $R_{10}$,$R_{12}$ and $R_{13}$ are as defined above; or —PO(O$C_1$-$C_8$alkyl)$_2$, or —$SiR_{14}R_{15}R_{16}$, wherein $R_{14}$, $R_{15}$ and $R_{16}$ independently of one another are H, $C_1$-$C_8$alkyl, $C_2$-$C_8$alkenyl, phenyl, $C_7$-$C_9$phenylalkyl, —O$C_1$-$C_8$alkyl, —O—$SiR_{17}R_{18}R_{19}$, wherein $R_{17}$, $R_{18}$ and $R_{19}$ are independently of each other H, $C_1$-$C_8$alkyl, $C_2$-$C_8$alkenyl, phenyl, $C_7$-$C_9$phenylalkyl, —O$C_1$-$C_8$alkyl; or —CH=CH-phenyl or —C($C_1$-$C_4$alkyl)=C($C_1$-$C_4$alkyl)-phenyl, phenyl-$C_1$-$C_4$alkyl, phenyl, naphthyl, biphenyl, $C_5$-$C_{12}$cycloalkyl or a 5- or 6-membered O-, S- or N-containing heterocyclic, ring;

benzophenonyl, thioxanthonyl;

or $R_1$ is $C_2$-$C_{18}$alkyl or $C_2$-$C_{18}$alkenyl which is interrupted by one or several non-successive —O—, —NH—, —$NR_{12}$- or —S—atoms, and may additionally be substituted once or more than once by groups selected from: halogen or CN, or —$OR_{10}$, —$SR_{10}$, —OCO—$R_{10}$, —COO—$R_{10}$, wherein $R_{10}$ is as defined above; or —$NR_{12}R_{13}$, —$N(R_{12})$—CO—$R_{10}$, —$N(R_{12})$—CO—$OR_{10}$, —$N(R_{12})$—CO—$NR_{12}R_{13}$, —$N(R_{12})$—CO-Hal, —CO—$NR_{12}R_{13}$, wherein $R_{10}$ and $R_{12}$ and $R_{13}$ are as defined above; or —$SO_2$—$R_{10}$, —$SO_2$—$OR_{10}$, —$SO_2$—$NR_{12}R_{13}$, wherein $R_{10}$, $R_{12}$ and $R_{13}$ are as defined above; or —PO(O$C_1$-$C_8$alkyl)$_2$, or —$SiR_{14}R_{15}R_{16}$, wherein $R_{14}$, $R_{15}$ and $R_{16}$ are as defined above; or phenyl-$C_1$-$C_4$alkyl, phenyl or $C_5$-$C_{12}$cycloalkyl;

or $R_1$ is $C_2$-$C_{18}$alkyl or $C_2$-$C_{18}$alkenyl which is interrupted by —CO—, —COO—, —OCO—, —OCOO—, —CO—N($R_{12}$)—, —N($R_{12}$)—CO—, —N($R_{12}$)—CO—N($R_{12}$)—, —N($R_{12}$)—COO—, —COO—$C_1$-$C_{18}$alkylene, —COS—$C_1$-$C_{18}$alkylene, —$SO_2$—, —$SO_2$—O—, —$SO_2$—N($R_{12}$)—, —($CH_3$)$_2$Si—[OSi($CH_3$)$_2$]$_{m'}$- with m'=1-6, phenyl-$C_1$-$C_4$alkylene, phenylene, naphthylene, biphenylene, $C_5$-$C_{12}$cycloalkylene or a 5- or 6-membered O-, S- or N-containing heterocyclic ring; wherein $R_{12}$ is as defined above;

or $R_1$ is trimethylsilyl or Hal-($CH_3$)$_2$Si—[OSi($CH_3$)$_2$]$_{m'}$- or ($CH_3$)$_3$Si—[OSi($CH_3$)$_2$]$_{m'}$- with m'=1-6; or $R_1$ is —COOH, —COO—$R_{10}$, —CO—$NR_{12}R_{13}$, —CO-vinyl, —CO-phenyl which is unsubstituted or substituted by one or more —$CH_3$, —$OCH_3$, —Cl; wherein $R_{10}$, $R_{12}$ and $R_{13}$ are as defined above; or $R_1$ is phenyl-$C_1$-$C_4$alkyl, phenyl, naphthyl, biphenyl, $C_5$-$C_{12}$cycloalkyl or a 5- or 6-membered O-, S- or N-containing heterocyclic ring; all of the radicals phenyl, naphthyl, biphenyl, $C_5$-$C_{12}$cycloalkyl or the 5- or 6-membered —O-, S- or N-containing heterocyclic ring being unsubstituted or substituted by one to five halogen, $C_1$-$C_8$alkyl, $C_1$-$C_8$alkylthio, $C_1$-$C_8$alkoxy and/or —$NR_{12}R_{13}$; wherein $R_{12}$ and $R_{13}$ are as defined above;

$R_1$ if n=2, is a divalent radical of the monovalent radical defined above or is

—$CH_2CH$=$CHCH_2$—, —$CH_2$—C≡C—$CH_2$—,

—$CH_2CH_2$—⟨phenyl⟩—$CH_2CH_2$—,

—$CH_2CH_2O$—⟨phenyl⟩—$OCH_2CH_2$— or

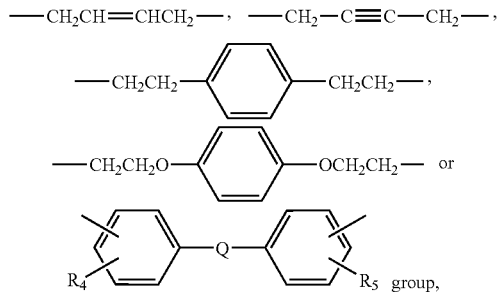

—$CH_2$—COO-Z-OCO—$CH_2$— wherein

Q is a single bond, —$CH_2$—, —$CR_6R_7$—, —O— or —S—; $R_4$ and $R_5$ are each independently of the other hydrogen, $C_1$-$C_4$alkyl or $C_1$-$C_4$alkoxy; $R_6$ and $R_7$ are each independently of the other $C_1$-$C_4$alkyl;

Z is $C_1$-$C_{18}$ alkylene or a bridge derived from a di,-tri,-tetra-or polyethylene glycol;

$R_2$ is $C_1$-$C_{18}$alkyl or $C_2$-$C_{18}$alkenyl; $C_1$-$C_{18}$alkyl or $C_2$-$C_{18}$alkenyl substituted once or more than once by halogen; or —$OR_{10}$, —$OCO$—$R_{10}$, —$OCO$-Hal, —$COO$—$R_{10}$, —$CH$=$CH$—$CO$—$OR_{10}$—$N(R_{12})$—$CO$—$R_{10}$, —$N(R_{12})$—$CO$-Hal,; —$C(C_1$-$C_4$alkyl)$=$C(C_1$-$C_4$alkyl)-$CO$—$OR_{10}$, —$CO$—$NR_{12}R_{13}$, wherein $R_{10}$, $R_{12}$ and $R_{13}$ are as defined above;

or —$CH$=$CH$-phenyl or —$C(C_1$-$C_4$alkyl)$=$C(C_1$-$C_4$alkyl)-phenyl; $C_3$-$C_{12}$cycloalkyl, $C_2$-$C_{18}$alkenyl, phenyl-$C_1$-$C_4$alkyl, phenyl, naphthyl, anthryl, biphenyl or a 5- or 6-membered —O-, S- or N-containing heterocyclic ring, the radicals phenyl, naphthyl, biphenyl or the 5- or 6-membered —O-, S- or N-containing heterocyclic ring being unsubstituted or substituted by one to five halogen, $C_1$-$C_8$alkyl, $C_1$-$C_8$alkoxy and/or $C_1$-$C_8$alkylthio;

$R_3$ is one of the radicals defined under $R_1$;

the process comprises the steps a) contacting elemental phosphorous or $P(Hal)_3$ with an alkali metal or an alkali earth metal optionally in the presence of a catalyst or an activator in a solvent to obtain metal phosphides $Me_3P$ or $Me'_3P_2$, wherein Me is an alkali metal and Me' is an alkali earth metal to obtain metal polyphosphides b) optionally adding an alcohol, optionally in the presence of a catalyst or an activator to obtain metal dihydrogen phosphides $MePH_2$;

c) subsequent acylation reaction with m acid halides of formula III or m carboxylic acid esters of formula IV

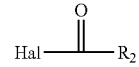  (III)

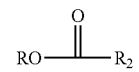  (IV)

or, in case that in formula I m=1, with one carboxylic ester of formula IV followed by one acid halide of formula III or vice versa, wherein R is the residue of an alcohol and $R_2$ is as defined above;

d) alkylation reaction in case of m=2, subsequent reaction with an electrophilic agent $R_1$Hal, $R_1$—$OSO_2$—O—$R_1$, $R_1$—$OSO_2$—$R_{20}$,

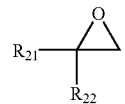

$(R_1$—O$)_3$PO, $H_2C$=$CR_{23}COOR_{10}$,

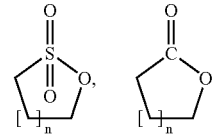

wherein $R_1$ and $R_{10}$ are as defined above, $R_{20}$ is $C_1$-$C_8$alkyl,, $C_1$-$C_8$perfluoroalkyl, aryl or $C_1$-$C_4$-alkylaryl, $R_{21}$ is H or $C_1$-$C_8$alkyl; $R_{22}$ is $C_1$-$C_{16}$alkyl or $C_2$-$C_{16}$alkenyl substituted once or more than once by halogen —$OR_{10}$, —$NR_{12}R_{13}$, —$SR_{10}$, —$OCO$—$R_{10}$, —$OCO$-Hal, —$COO$—$R_{10}$, —$N(R_{12})$—CO—$R_{10}$, —$N(R_{12})$—CO—$OR_{10}$, —$N(R_{12})$—CO—$NR_{12}R_{13}$, —$N(R_{12})$—CO-Hal, —CO—$NR_{12}R_{13}$, —$SO_2$—$R_{10}$, —$SO_2$—$OR_{10}$, —$SO_2$—$NR_{12}R_{13}$, —CH=CH—CO—$OR_{10}$, —CH=CH-phenyl, —$C(C_1$-$C_4$alkyl)$=$C(C_1$-$C_4$alkyl)-CO—$OR_{10}$ or —$C(C_1$-$C_4$alkyl)$=$C(C_1$-$C_4$alkyl)-phenyl, phenyl-$C_1$-$C_4$alkyl, phenyl, naphthyl, biphenyl, $C_5$-$C_{12}$cycloalkyl or a 5- or 6-membered O-, S- or N-containing heterocyclic ring;

$R_{23}$ is H or $CH_3$, and n=1-5 and $R_{10}$, $R_{12}$ and $R_{13}$ is as defined above and in the case of m=1 reaction with an electrophilic agent $R_1$Hal, $R_1$—$OSO_2$—O—$R_1$, $R_1$—$OSO_2$—$R_{20}$,

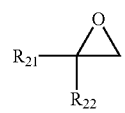

$(R_1$—O$)_3$PO, $H_2C$=$CR_{23}COOR_{10}$,

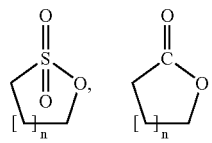

wherein $R_1$ and $R_{10}$; $R_{20}$, $R_{21}$, $R_{22}$ and $R_{23}$ are as defined above or other electrophilic agents followed by the reaction with an electrophilic agent $R_3Hal$ $R_3$—$OSO_2$—O—$R_3$, $R_3$—$OSO_2$—$R_{20}$,

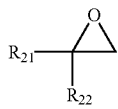

$(R_3$—$O)_3PO$, $H_2C$=$CR_{23}COOR_{10}$,

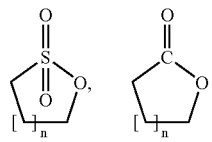

wherein $R_3$ and $R_{10}$, $R_{20}$, $R_{21}$, $R_{22}$ and $R_{23}$ are as defined above, to obtain the compounds of formula I.

2. A process according to claim 1 for the preparation of monoacyl-phosphanes of the formula I' (compounds of the formula I with n=1 and m=1)

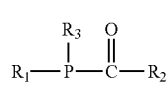
(I')

which process comprises the steps a), b) and c); and
d) reaction with an electrophilic agent $R_1Hal$ or other electrophilic agents containing the residue $R_1$ as defined for m=1 followed by the reaction with an electrophilic agent $R_3Hal$ or other electrophilic agents containing the residue $R_3$ as defined for m=1 to obtain the compounds of formula I'.

3. A process according to claim 1 for the preparation of symmetric bisacylphosphanes of the formula I" (compounds of the formula I with n=1 and m=2)

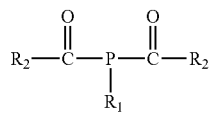
(I")

which process comprises the steps a), b) and c) as defined for m=2; and
d) reaction with an electrophilic agent $R_1Hal$ or other electrophilic agents containing the residue $R_1$ as defined for m=2 to obtain the compounds of formula I".

4. A process according to claim 1 for the preparation of unsymmetric bisacylphosphanes of the formula I'"(compounds of the formula I with n=1 and m=2)

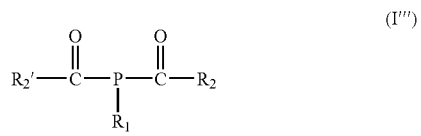
(I'")

wherein $R_2$ and $R_2'$ independently of one another are as defined for $R_2$ with the proviso that $R_2$ is not equal $R_2'$, which process comprises the steps a) and b); and
c) subsequent reaction with an acid halide of formula III or a carboxylic acid ester of formula IV

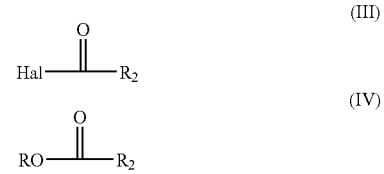

wherein R is the residue of an alcohol; then subsequent reaction with a second acid halide III' or a second carboxylic acid ester of the formula IV',

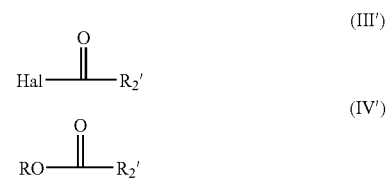

and
d) reaction with an electrophilic agent $R_1Hal$ or other electrophilic agents containing the residue $R_1$ as defined for m=2
to obtain the compounds of formula I'".

5. A process according to claim 1, wherein n=1 and
$R_1$ is phenyl, linear or branched $C_1$-$C_8$alkyl or $C_2$-$C_{18}$alkenyl or is linear or branched $C_1$-$C_8$alkyl or $C_2$-$C_{18}$alkenyl substituted by CN, trifluormethyl, oxiranyl, isoindole-1,3-dione, —O—$C_1$-$C_{18}$alkyl, —O—benzyl, —CO-phenyl, —CO—$C_1$-$C_{18}$alkyl, —OCO—$C_1$-$C_{18}$alkyl; —OCO—$C_1$-$C_{18}$alkenyl; —COO—$C_1$-$C_{18}$alkyl;
—COO—$C_1$-$C_{18}$alkylene-phenyl, —COO—$C_1$-$C_{18}$alkylene-cycloalkyl, —COO—$C_1$-$C_{18}$alkylene-tetrahydrofuranyl, —COO—$C_1$-$C_{18}$alkylene-furanyl, —COO—cycloalkyl, —COO—$C_1$-$C_{18}$alkenyl; —COO—$C_1$-$C_{18}$alkenylene-phenyl; —COO—$(CH_2)_{2-3}$—Cl, —COO—$[(CH_2)_{2-3}$—$O]_{1-10}$—$C_1$-$C_6$alkyl; —COO—$[(CH_2)_{2-3}$—$O]_{1-10}$—$C_1$-$C_6$—OH, —CO—$CH_2$—CO—$C_1$-$C_{18}$alkyl; —CO—$CH_2$—COO—$C_1$-$C_{18}$alkyl, —O-tetrahydropyranyl, bicyclo [2.2.1]hept-2-en-5-yl)-methyl, $PO(OC_1$-$C_6$alkyl$)_2$ and
wherein $R_2$ is phenyl which is substituted in 2,6- or 2,4,6-position by $C_1$-$C_4$alkyl and/or $C_1$-$C_4$alkoxy, and/or chlorine; 2-ethoxy-naphth-1-yl, 2-methyl-naphth-1-yl or anthr-9-yl.

6. A process according to claim 1 which process comprises, as an additional step, oxidation or reaction with sulfur of the acylphosphane of formula I for the preparation of (bis)acylphosphane oxides and (bis)acylphosphane sulfides of formula IV

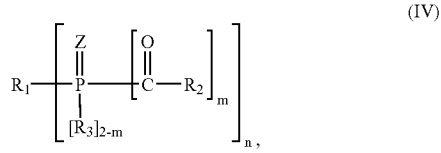

wherein
Z is O or S.

7. A process according to claim 1 for the preparation of (bis)acylphosphanes of formula I, the process comprising the steps of:

a) contacting red phosphorous or $PCl_3$ with an alkali metal in the presence of a solvent and optionally in the presence of polycyclic hydrocarbon catalyst, b) adding a sterically hindered alcohol;

c) subsequent reaction with two equivalents of an acid halide Hal-CO—$R_2$ to obtain a metal bisacylphosphide [$R_2$—CO—P=C(OMe)$R_2$], wherein Me is Na or Li; or with one equivalent of a caboxylic acid ester RO—CO—$R_2$, followed by one equivalent of an acid halide Hal-CO—$R_2$' to obtain a metal bisacylphosphide [$R_2$—CO—P=C(OMe)$R_2$'], wherein Me is an alkali metal d) subsequent reaction with an electrophilic agent $R_1$Hal or $R_1OSO_2OR_1$, to obtain the compounds of formula I.

8. A process according to claim 7, wherein in step a) sodium in liquid ammonia is contacted with red phosphorus in tetrahydrofuran.

* * * * *